(12) United States Patent
Wiesner et al.

(10) Patent No.: US 6,743,810 B2
(45) Date of Patent: Jun. 1, 2004

(54) INDOL-3-YL DERIVATIVES

(75) Inventors: Matthias Wiesner, Reinheim (DE);
Simon Goodman, Griesheim (DE);
Rudolf Gottschlich, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/203,406

(22) PCT Filed: Jan. 5, 2001

(86) PCT No.: PCT/EP01/00084

§ 371 (c)(1),
(2), (4) Date: Aug. 9, 2002

(87) PCT Pub. No.: WO01/58893

PCT Pub. Date: Aug. 16, 2001

(65) Prior Publication Data

US 2003/0045728 A1 Mar. 6, 2003

(30) Foreign Application Priority Data

Feb. 11, 2000 (DE) .......................................... 100 06 139

(51) Int. Cl.[7] ................. A61K 31/4439; A61K 31/404; C07D 401/00; C07D 277/02; A61P 9/00
(52) U.S. Cl. ..................... 514/339; 514/422; 546/277.4; 548/152; 548/204; 548/465; 548/506; 548/509
(58) Field of Search ............................. 546/277.4, 465, 546/152; 548/506, 204, 509; 514/339, 422

(56) References Cited

FOREIGN PATENT DOCUMENTS

| EP | 498268 | * 8/1992 |
|----|--------|----------|
| WO | 94 12478 | 6/1994 |
| WO | 97 37655 | 10/1997 |
| WO | 99 33798 | 7/1999 |

* cited by examiner

*Primary Examiner*—Joseph K. McKane
*Assistant Examiner*—Robert Shiao
(74) *Attorney, Agent, or Firm*—Millen, White, Zelano, Branigan, P.C.

(57) ABSTRACT

Indol-3-yl derivatives of the general formula I

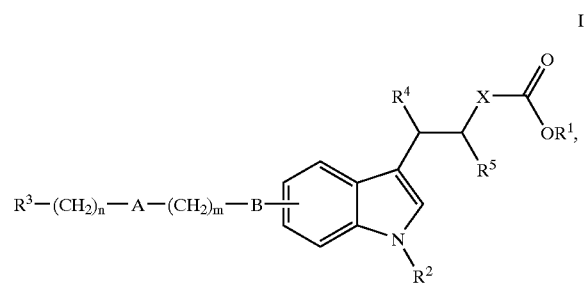

in which A, B, X, $R^1$, $R^2$, $R^3$, $R^4$, $R^5$, n and m are as defined in patent claim 1, and their physiologically acceptable salts or solvates are integrin inhibitors and can be employed for combating thromboses, cardiac infarction, coronary heart diseases, arteriosclerosis, inflammations, tumours, osteoporosis, rheumatic arthritis, macular degenerative disease, diabetic retinopathy, infections and restenosis after angioplasty or in pathological processes maintained or propagated by angiogenesis.

19 Claims, No Drawings

INDOL-3-YL DERIVATIVES

This application is a 371 of PCT/EP01/00084 filed on Jan. 5, 2001.

The invention relates to indol-3-yl derivatives of the formula I

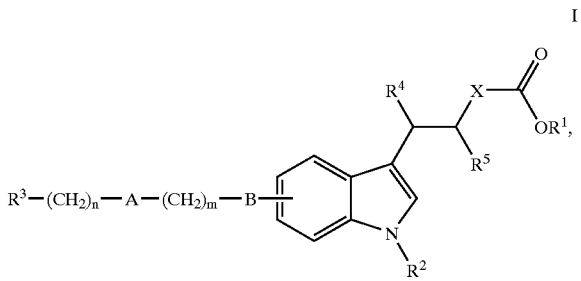

in which

A and B are each, independently of one another, O, S, NH, $NR^7$, CO, CONH, NHCO or a direct bond, X is alkylene having 1 to 2 carbon atoms which is unsubstituted or monosubstituted by $R^4$ or $R^5$, or a direct bond, $R^1$ is H, Z or $-(CH_2)_o-Ar$, $R^2$ is H, $R^7$ or $-C(O)Z$, $R^3$ is $NHR^6$, $-NR^6-C(=NR^6)-NHR^6$, $-C(=NR^6)-NHR^6$, $-NR^6-C(=NR^9)-NHR^6$, $-C(=NR^9)-NHR^6$ or $Het^1$, $R^4$ and $R^5$ are each, independently of one another, H, oxo, $R^7$, $-(CH_2)_o-Ar$, $-C(O)-(CH_2)_o-Ar$, $-C(O)-(CH_2)_o-R^7$, $-C(O)-(CH_2)_o-Het$, Het, $NHR^6$, NHAr, NH—Het, $CONH-R^7$, $CONH-(CH_2)_o-Ar$, $CONH-(CH_2)_o-Het$, $OR^7$, OAr, $OR^6$ or O—Het, $R^6$ is H, $-C(O)R^7$, $-C(O)-Ar$, $-C(O)-Het$, $R^7$, $COOR^7$, $COO-(CH_2)_o-Ar$, $COO-(CH_2)_o-Het$, $SO_2-Ar$, $SO_2R^7$ or $SO_2-Het$, $R^7$ is alkyl having 1 to 10 carbon atoms or cycloalkyl having 3 to 10 carbon atoms, $R^8$ is Hal, $NO_2$, CN, Z, $-(CH_2)_o-Ar$, $COOR^1$, $OR^1$, $CF_3$, $OCF_3$, $SO_2R^1$, $NHR^1$, $N(R^1)_2$, $NH-C(O)R^1$, $NHCOOR^1$, COOH, COOZ or $C(O)R^1$, $R^9$ is CN or $NO_2$, Z is alkyl having 1 to 6 carbon atoms, Ar is aryl which is unsubstituted or monosubstituted or polysubstituted by $R^8$, Hal is F, Cl, Br or I, Het is a saturated, partially or fully unsaturated monocyclic or bicyclic heterocyclic radical having 5 to 10 ring members, where 1 or 2 N and/or 1 or 2 S or O atoms may be present and the heterocyclic radical may be monosubstituted or disubstituted by $R^8$, $Het^1$ is a saturated, partially or fully unsaturated monocyclic or bicyclic heterocyclic radical having 5 to 10 ring members and 1 to 4 N atoms which may be unsubstituted or monosubstituted or disubstituted by Hal, $R^7$, $OR^7$, CN, NHZ, oxo or $NO_2$, n is 0, 1 or 2, m is 0, 1, 2, 3, 4, 5 or 6, and o is 0, 1 or 2, and their physiologically acceptable salts and solvates.

Some similar compounds are disclosed in WO 99/30713 and WO 94/12478.

The object of the invention was to discover novel compounds having valuable properties, in particular those which are used for the preparation of medicaments.

It has been found that the compounds of the formula I and their salts are well tolerated and have very valuable pharmacological properties. In particular, they act as integrin inhibitors, inhibiting, in particular, the interactions of the αv-, β3- and β5-integrin receptors with ligands, such as, for example, the binding of vitronectin to the integrin receptor. Integrins are membrane-bound, heterodimeric glycoproteins consisting of an α subunit and a smaller β subunit. The relative affinity and specificity for ligand binding is determined by recombination of the various α and β subunits. Particular efficacy is exhibited by the compounds according to the invention in the case of integrins αvβ1, αvβ3, αvβ5, αIIbβ3, αvβ6 and αvβ8, preferably αvβ3, αvβ5 and αIIbβ3. The compounds according to the invention are particularly potent inhibitors of the vitronectin receptor αvβ3 and/or αvβ5 and/or of the fibrinogen receptor αIIbβ3. The compounds according to the invention are particularly preferably inhibitors of the vitronectin receptor αvβ3.

An essential factor for the activity of integrin inhibitors is the presence of an acid function at a suitable distance from a base centre. The activity and specificity can be controlled by adjusting the spacer length and the type of the base centre. A suitable central template is indole.

αvβ3 integrin is expressed in a number of cells, for example endothelium cells, cells of smooth vascular muscles, for example the aorta, cells for breaking down bone matrix (osteoclasts) or tumour cells.

The action of the compounds according to the invention can be demonstrated, for example, by the method described by J. W. Smith et al. in J. Biol. Chem. 1990, 265, 12267–12271.

B. Felding-Habermann and D. A. Cheresh in Curr. Opin. Cell. Biol. 1993, 5, 864, describe the significance of the integrins as adhesion receptors for a wide variety of phenomena and clinical pictures, especially in relation to the vitronectin receptor αvβ3.

The dependence of formation of angiogenesis on the interaction between vascular integrins and extracellular matrix proteins has been described by P. C. Brooks, R. A. Clark and D. A. Cheresh in Science 1994, 264, 569–571.

The possibility of inhibiting this interaction and so initiating apoptosis (programmed cell death) of angiogenic vascular cells by a cyclic peptide has been described by P. C. Brooks, A. M. Montgomery, M. Rosenfeld, R. A. Reisfeld, T. Hu, G. Klier and D. A. Cheresh in Cell 1994, 79, 1157–1164. In this, for example, αvβ3 antagonists or antibodies against αvβ3 were described which cause shrinkage of tumours due to the initiation of apoptosis.

The experimental evidence that the compounds according to the invention also prevent the attachment of living cells to the corresponding matrix proteins and accordingly also prevent the attachment of tumour cells to matrix proteins can be provided in a cell adhesion test analogously to the method of F. Mitjans et al., J. Cell Science 1995, 108, 2825–2838.

P. C. Brooks in J. Clin. Invest. 1995, 96, 1815–1822, describe $α_vβ3$ antagonists for combating cancer and for the treatment of tumour-induced angiogenic diseases.

The compounds are able to inhibit the binding of metal proteinases to integrins and thus prevent the cells utilizing the enzymatic activity of the proteinase. An example can be found in the ability of a cyclo-RGD peptide to inhibit the binding of MMP-2 (matrix-metallo-proteinase-2) to the vitronectin receptor αvβ3, as described in P. C. Brooks et al., Cell 1996, 85, 683–693.

The compounds of the formula I according to the invention can therefore be employed as medicament active ingredients, in particular for the treatment of tumour diseases, osteoporosis, osteolytic diseases and for suppressing angiogenesis.

Compounds of the formula I which block the interaction of integrin receptors and ligands, such as, for example, of fibrinogen to the fibrinogen receptor (glycoprotein IIb/IIIa or αIIβ3), prevent the spread of tumour cells by metastasis and can therefore be employed as antimetastatic substances in operations in which tumours are removed or attacked surgically. This is confirmed by the following observations:

The spread of tumour cells from a local tumour into the vascular system occurs through the formation of microaggregates (microthromboses) due to the interaction of the tumour cells with blood platelets. The tumour cells are masked by the protection in the microaggregate and are not recognized by the immune system cells. The microaggregates are able to attach to vessel walls, simplifying further penetration of tumour cells into the tissue. Since the formation of microthromboses is promoted by ligand binding to the corresponding integrin receptors, for example αvβ3 or αIIbβ3, on activated blood platelets, the corresponding antagonists can be regarded as effective metastasis inhibitors.

Besides the binding of fibrinogen, fibronectin and von Willebrand factor to the fibrinogen receptor of blood platelets, compounds of the formula I also inhibit the binding of further adhesive proteins, such as victronectin, collagen and laminin, to the corresponding receptors on the surface of various types of cell. In particular, they prevent the formation of blood platelet thromboses and can therefore be employed for the treatment of thromboses, apoplexia, cardiac infarction, inflammations and arteriosclerosis.

The thrombocyte aggregation-inhibiting action can be demonstrated in vitro by the method of Born (Nature 1962, 4832, 927–929).

The compounds of the formula I can be employed as medicament active ingredients in human and veterinary medicine, in particular for the prophylaxis and/or therapy of circulation disorders, thromboses, cardiac infarction, arteriosclerosis, apoplexia, angina pectoris, tumour diseases, such as tumour development or tumour metastasis, osteolytic diseases, such as osteoporosis, pathologically angiogenic diseases, such as, for example, inflammations, opthalmological diseases, diabetic retinopathy, macular degeneration, myopia, ocular histoplasmosis, restenosis, rheumatic arthritis, osteo-arthritis, rubeotic glaucoma, ulcerative colitis, Crohn's disease, atherosclerosis, psoriasis, restenosis after angioplasty, multiple sclerosis, viral infection, bacterial infection, fungal infection, in acute kidney failure and in wound healing for supporting the healing process.

The compounds of the formula I can be employed as antimicrobial substances in operations where biological materials, implants, catheters or cardiac pacemakers are used. They have an antiseptic action here. The efficacy of the antimicrobial activity can be demonstrated by the method described by P. Valentin-Weigund et al. in Infection and Immunity, 1988, 2851–2855.

A measure of the uptake of a medicament active ingredient in an organism is its bioavailability.

If the medicament active ingredient is administered to the organism intravenously in the form of an injection solution, its absolute bioavailability, i.e. the proportion of the pharmaceutical species which is unchanged in the systemic blood, i.e. enters the general circulation, is 100%. On oral administration of a therapeutic active ingredient, the active ingredient is generally in the form of a solid in the formulation and must therefore first dissolve in order that it can overcome the entry barriers, for example the gastrointestinal tract, the oral mucous membrane, nasal membranes or the skin, in particular the stratum corneum, and can be absorbed by the body. Pharmacokinetic data, i.e. on the bioavailability, can be obtained analogously to the method of J. Shaffer et al., J. Pharm. Sciences, 1999, 88, 313–318.

The invention relates to the compounds of the formula I according to claim 1 and their physiologically acceptable salts and/or solvates as therapeutic active ingredients.

The invention accordingly relates to compounds of the formula I according to claim 1 and their physiologically acceptable salts and/or solvates as αv-integrin inhibitors.

The invention furthermore relates to compounds of the formula I according to claim 1 and their physiologically acceptable salts and/or solvates as GPIIb/IIIa antagonists.

The invention relates to compounds of the formula I according to claim 1 and their physiologically acceptable salts and/or solvates for use in combating diseases.

The compounds of the formula I have at least one centre of chirality and can therefore occur in a number of stereoisomeric forms. All of these forms (for example D and L forms) and their mixtures (for example the DL forms) are included in the formula.

The compounds according to the invention according to claim 1 also cover so-called prodrug derivatives, i.e. compounds of the formula I modified with, for example, alkyl or acyl groups, sugars or oligopeptides, which are rapidly cleaved in the organism to give the effective compounds according to the invention.

Furthermore, free amino groups or free hydroxyl groups can be provided as substituents of compounds of the formula I with corresponding protecting groups.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and their salts and solvates according to claim 1 and to a process for the preparation of compounds of the formula I and their salts and solvates, characterized in that
 a) a compound of the formula I is liberated from one of its functional derivatives by treatment with a solvolyzing or hydrogenolyzing agent, or
 b) a radical $R^1$, $R^2$, $R^3$, $R^4$, $R^5$ and/or $R^6$ is converted into another radical $R^1$, $R^2$, $R^3$, $R^4$, $R^5$ and/or $R^6$ for example by
  i) converting an amino group into a guanidino group by reaction with an amidating agent,
  ii) saponifying an ester,
  iii) alkylating or acylating an amino group,
  iv) converting a cyano group into an amidino group,
 and/or a base or acid of the formula I is converted into one of its salts.

In the formulae above, Z is alkyl, which is linear or branched and has 1 to 6, preferably 1, 2, 3, 4, 5 or 6, carbon atoms. Z is preferably methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Z is particularly preferably methyl or ethyl.

Alkyl having 1 to 10 carbon atoms may be linear or branched and preferably has 1, 2, 3, 4, 5, 6, 7, 8, 9 or 10 carbon atoms. Alkyl having 1 to 10 carbon atoms is preferably methyl, furthermore ethyl, n-propyl, isopropyl, n-butyl, sec-butyl or tert-butyl, furthermore also n-pentyl, 1-, 2- or 3-methylbutyl, n-hexyl, 1-, 2-, 3- or 4-methylpentyl, n-heptyl, n-octyl, n-nonyl or n-decyl.

Alkylene having 1 to 2 carbon atoms is methylene or ethylene, where at least one C—H bond of the alkylene may be replaced by a C—$R^4$ or C—$R^5$ bond.

Ar is aryl which is unsubstituted or monosubstituted, disubstituted or trisubstituted by $R^8$, where aryl is phenyl, naphthyl, anthryl or biphenyl. Ar is preferably phenyl, naphthyl or biphenyl, each of which is unsubstituted or monosubstituted, disubstituted or trisubstituted by $R^8$. Ar is particularly preferably phenyl or biphenyl-4-yl, each of which is unsubstituted or monosubstituted or polysubstituted by $R^8$.

Ar is therefore preferably phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m-, p-trifluoromethylphenyl, o-, m-, p-trifluoromethoxyphenyl, o-, m- or p-fluorophenyl, o-, m- or p-chlorophenyl, o-, m- or p-bromophenyl, o-, m- or p-carboxyphenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 3-chloro-4-fluorophenyl, 4-chloro-3-trifluoromethylphenyl, 3-fluoro-4-trifluoromethylphenyl, 4-fluoro-2-hydroxyphenyl, 2,4,6-trifluorophenyl, 2-chloro-3,6-difluorophenyl, 3-cyano-4-dimethylamino-2-fluorophenyl or biphenyl-4-yl, naphthalen-1-yl, naphthalen-2-yl or 2-, 3-, 4-, 5-, 6-, 7- or 8-methylnaphthalen-1-yl, 2-, 3-, 4-, 5-, 6-, 7- or 8-ethylnaphthalen-1-yl, 2-, 3-, 4-, 5-, 6-, 7- or 8-chloronaphthalen-1-yl, 2-, 3-, 4-, 5-, 6-, 7- or 8-fluoronaphthalen-1-yl, 2-, 3-, 4-, 5-, 6-, 7- or 8-bromonaphthalen-1-yl, 2-, 3-, 4-, 5, 6-, 7- or 8-hydroxynaphthalen-1-yl, 1-, 3-, 4-, 5-, 6-, 7- or 8-methylnaphthalen-2-yl, 1-, 3-, 4-, 5-, 6-, 7- or 8-ethylnaphthalen-2-yl, 1-, 3-, 4-, 5-, 6-, 7, or 8-chloronaphthalen-2-yl, 1-, 3-, 4-, 5-, 6-, 7- or 8-fluoronaphthalen-2-yl, 1-, 3-, 4-, 5-, 6-, 7- or 8-bromonaphthalen-2-yl, 1-, 3-, 4-, 5-, 6-, 7 or 8-hydroxynaphthalen-2-yl.

Ar is particularly preferably phenyl, m- or p-trifluoromethoxyphenyl, p-isopropylphenyl, p-fluorophenyl, m-chlorophenyl, m-hydroxyphenyl, p-carboxyphenyl, 2,4- or 3,5-dichlorophenyl, 4-chloro-3-trifluoromethylphenyl, 2,6-, 3,4- or 3,5-difluorophenyl, 3-fluoro-4-trifluoromethylphenyl, 2,4,6-trifluorophenyl, 2-chloro-3,6-difluorophenyl, 3-cyano-4-dimethylamino-2-fluorophenyl or biphenyl-4-yl. Ar is very particularly preferably p-fluorophenyl.

C(O)Z is alkanoyl and is preferably formyl, acetyl, propionyl, butyryl, pentanoyl or hexanoyl.

C(O)—Ar is aroyl, where Ar is as defined above. Particular preference is given to benzoyl.

COO—$(CH_2)_o$—Ar is arylalkyloxycarbonyl, where —$(CH_2)_o$—Ar is as defined below. Particular preference is given to benzyloxycarbonyl.

Cycloalkyl having 3 to 10 carbon atoms is preferably cyclopropyl, cyclobutyl, cyclopentyl, cyclohexyl, cycloheptyl or cyclooctyl. Cycloalkyl is likewise a monocyclic or bicyclic terpene, preferably p-menthane, menthol, pinane, bornane or camphor, where each known stereoisomeric form is included, or adamantyl. For camphor, this is both L-camphor and D-camphor.

—$(CH_2)_o$—Ar is preferably Ar for o=0 or benzyl, phenylethyl or naphthylmethyl for o=1 or 2. —$(CH_2)_o$—Ar is particularly preferably benzyl for o=1 or Ar for o=0.

Hal is F, Cl, Br or 1, particularly preferably F, Cl or Br.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4 or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7- benzofuryl, 2-3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 4- or 5-benzothiadiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or fully hydrogenated. Het can thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6- or -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

Het is preferably Z-substituted or unsubstituted morpholin-4-yl, tetrahydropyran-4-yl, piperidin-4-yl, indol-2-yl, pyrrol-2-yl, pyridin-4-yl, thiophen-2-yl, thiazol-2-yl or benzothiadiazol-5-yl. Het is particularly preferably unsubstituted indol-2-yl, pyrrol-2-yl, pyridin-4-yl, thiophen-2-yl, thiazol-2-yl or benzothiadiazol-5-yl.

$Het^1$ is preferably substituted or unsubstituted 1-, 2- or 3-pyrrolyl, 1-, 2-, 4- or 5-imidazolyl, 3-, 4- or 5-pyrazolyl, 2-, 3- or 4-pyridyl, 2-, 4-, 5- or 6-pyrimidinyl, furthermore preferably 3- or 4-pyridazinyl, pyrazinyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 1-, 2-, 3-, 4-, 5-, 6-, 7- or 8-quinolinyl, 1-, 3-, 4-, 5-, 6-, 7- or 8-isoquinolinyl, 3-, 4-, 5-, 6-, 7- or 8-cinnolinyl, 1-, 4-, 5-, 6-, 7- or 8-phthalazinyl, 2-, 3-, 5-, 6-, 7- or 8-quinoxalinyl, 2-, 4-, 5-, 6-, 7- or 8-quinazolinyl. The heterocyclic radicals may also be partially or fully hydrogenated. $Het^1$ can thus also be 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6-, -7-1H-indolyl, 2,3-dihydro-1-, -2-, -3, -4- or -5-pyrazolyl, tetrahydro-1-, -3- or -4-pyrazolyl, 1,5-dihydroimidazol-4-on-2- or -5-yl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3, -4-, -5- or -6-pyridyl, 1-, 2-, 3- or 4-piperidinyl, 1-, 2-, 3- or 4-azepanyl, tetrahydro-2-, -3- or -4-pyranyl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

The said heterocyclic rings may also be monosubstituted or disubstituted by =O or NHZ.

Het[1] is particularly preferably 3-nitropyridin-2-yl, 3-aminopyridin-2-yl, 3-(N-acetylamino)pyridin-2-yl, pyridin-2-yl, 1,4,5,6-tetrahydropyridin-2-yl, benzimidazol-2-yl, imidazol-2-yl, 4,5-dihydroimidazol-2-yl, 3,5-dihydroimidazol-4-on-2-yl, pyrimidin-2-yl or 1,4,5,6-tetrahydropyrimidin-2-yl.

A and B are each, independently of one another, O, S, NH, NR$^7$, CO, CONH, NHCO or a direct bond, where R$^7$ is as defined below. A is particularly preferably NH, CONH, NHCO or a direct bond, very particularly preferably NH. B is particularly preferably O or a direct bond, very particularly preferably O.

X is alkylene having 1 to 2 carbon atoms which is unsubstituted or mono-substituted by R$^4$ or R$^5$, where R$^4$ and R$^5$ are as defined below, or a direct bond. X is particularly preferably a bond or phenyl-substituted methylene. X is very particularly preferably a direct bond.

m is 0, 1, 2, 3, 4, 5 or 6. m is particularly preferably 3 or 4. m is very particularly preferably 3.

n is 0, 1 or 2. n is particularly preferably 0.

o is 0, 1 or 2, preferably 0 or 1, particularly preferably 0

R$^1$ is H, Z or —(CH$_2$)$_o$—Ar, where Z, o and —(CH$_2$)$_o$—Ar are as defined above.

R$^1$ is particularly preferably H.

R$^2$ is H, R$^7$ or —C(O)Z, where R$^7$ is as defined below, and Z is as defined above. R$^2$ is particularly preferably H, methyl or acetyl. R$^2$ is very particularly preferably H.

R$^3$ is NHR$^6$, —NR$^6$—C(=NR$^6$)—NHR$^6$, —C(=NR$^6$)—NHR$^6$, —NR$^6$—C(=NR$^9$)—NHR$^6$, —C(=NR$^9$)—NHR$^6$ or Het$^1$, where R$^6$ is as defined below and Het$^1$ is as defined above. R$^3$ is preferably amino, guanidino, NHBoc, —C(=N-Boc)-NHBoc, —NH—C(=N-Boc)-NHBoc, NBoc-C(=N-Boc)-NH$_2$, where Boc is tert-butoxycarbonyl, —NH—C(=N—CN)—NR$^6$ or —NH—C(=N—NO$_2$)—NR$^6$, where R$^6$ is as defined below, or 3-nitropyridin-2-yl, 3-aminopyridin-2-yl, 3-(N-acetylamino)pyridin-2-yl, pyridin-2-yl, 1,4,5,6-tetrahydropyridin-2-yl, benzimidazol-2-yl, imidazol-2-yl, 4,5-dihydroimidazol-2-yl, 3,5-dihydroimidazol-4-on-2-yl, pyrimidin-2-yl or 1,4,5,6-tetrahydropyrimidin-2-yl. R$^3$ is particularly preferably 1H-imidazol-2-yl, 4,5-dihydroimidazol-2-yl, 3,5-dihydroimidazol-4-on-2-yl or pyridin-2-yl.

R$^4$ and R$^5$ are each, independently of one another, H, oxo, R$^7$, —(CH$_2$)$_o$—Ar, —C(O)—(CH$_2$)$_o$—Ar, —C(O)—(CH$_2$)$_o$R$^7$, —C(O)—(CH$_2$)$_o$—Het, Het, NHR$^6$, NHAr, NH—Het, CONH—R$^7$, CONH—(CH$_2$)$_o$—Ar, CONH—(CH$_2$)$_o$—Het, OR$^7$, OAr, OR$^6$ or O—Het, where Ar and Het are as defined above, and R$^6$ and R$^7$ are as defined below.

—C(O)—(CH$_2$)$_o$—Ar is preferably phenylcarbonyl, benzylcarbonyl or phenylethylcarbonyl.

In —C(O)—(CH$_2$)$_o$—R$^7$, R$^7$ is as defined below. —C(O)—(CH$_2$)$_o$—R$^7$ is preferably acetyl, propionyl, butanoyl, cyclohexylcarbonyl, cyclopentylcarbonyl, cyclohexylmethylcarbonyl or cyclohexylethylcarbonyl.

In —C(O)—(CH$_2$)$_o$—Het, Het is as defined above. —C(O)—(CH$_2$)$_o$—Het is preferably pyridin-4-ylcarbonyl, pyridin-4-ylmethylcarbonyl or pyridin-4-yl-ethylcarbonyl.

In CONH—R$^7$, R$^7$ is as defined below. —CONH—R$^7$ is preferably methylaminocarbonyl, ethylaminocarbonyl, cyclohexylaminocarbonyl, cyclopentylaminocarbonyl, cyclohexylmethylaminocarbonyl or cyclohexylethylaminocarbonyl. CONH—(CH$_2$)$_o$—Ar is preferably phenylaminocarbonyl, benzylaminocarbonyl or phenylethylaminocarbonyl.

CONH—(CH$_2$)$_o$—Het is preferably pyridin-4-ylaminocarbonyl, pyridin-4-yl-methylaminocarbonyl or pyridin-4-ylethylaminocarbonyl.

R$^4$ and R$^5$ are preferably each, independently of one another, H, —(CH$_2$)$_o$—Ar, R$^7$ or Het, where o is 0 or 1. R$^4$ is particularly preferably phenyl, 3-trifluoromethoxyphenyl, 4-fluorophenyl, 3-chlorophenyl, 3-hydroxyphenyl, pyridin-4-yl, 3,5-dichlorophenyl, 2,4-dichlorophenyl, cyclohexyl, 4-chloro-3-trifluoromethylphenyl, benzothiadiazol-4-yl, 2,6-difluorophenyl, 2-chloro-3,6-difluorophenyl, 2,4,6-trifluorophenyl or cyclohexyl. R$^5$ is particularly preferably H.

R$^6$ is preferably H, —C(O)R$^7$, —C(O)—Ar, R$^7$, COOR$^7$, COO—(CH$_2$)$_o$—Ar, SO$_2$—Ar, SO$_2$R$^7$ or SO$_2$—Het, where Ar and Het are as defined above, and R$^7$ is alkyl having 1 to 10 carbon atoms or cycloalkyl having 3 to 10 carbon atoms. R$^6$ is preferably H, methoxycarbonyl, ethoxycarbonyl, tert-butoxycarbonyl or benzyloxycarbonyl.

R$^7$ is alkyl having 1 to 10 carbon atoms or cycloalkyl having 3 to 10 carbon atoms, where the terms alkyl and cycloalkyl are as defined above. R$^7$ is preferably tert-butyl, 2,2-dimethylpropyl, cyclopropyl or cyclohexyl.

R$^8$ is Hal, NO$_2$, CN, Z, —(CH$_2$)$_o$—Ar, COOR$^1$, OR$^1$, CF$_3$, OCF$_3$, SO$_2$R$^1$, NHR$^1$, N(R$^1$)$_2$, NH—C(O)R$^1$, NHCOOR$^1$ or C(O)R$^1$, where Hal, Z, —(CH$_2$)$_o$—Ar and R$^1$ are as defined above.

R$^9$ is CN or NO$_2$, particularly preferably CN.

Preferred versions of the substituent R$^3$—(CH$_2$)$_n$—A—(CH$_2$)$_m$—B— are

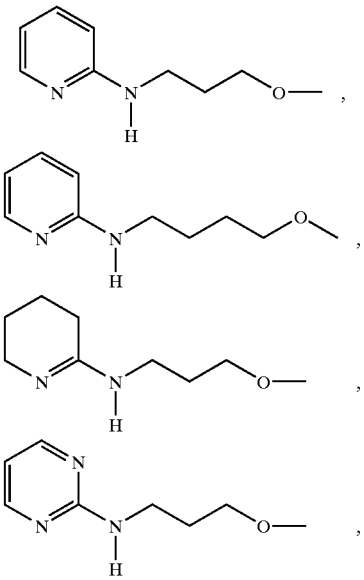

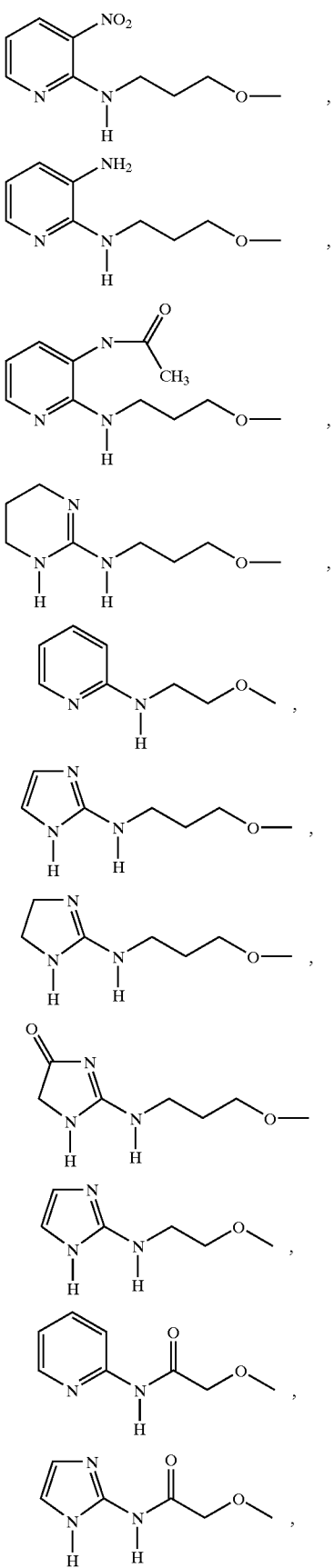

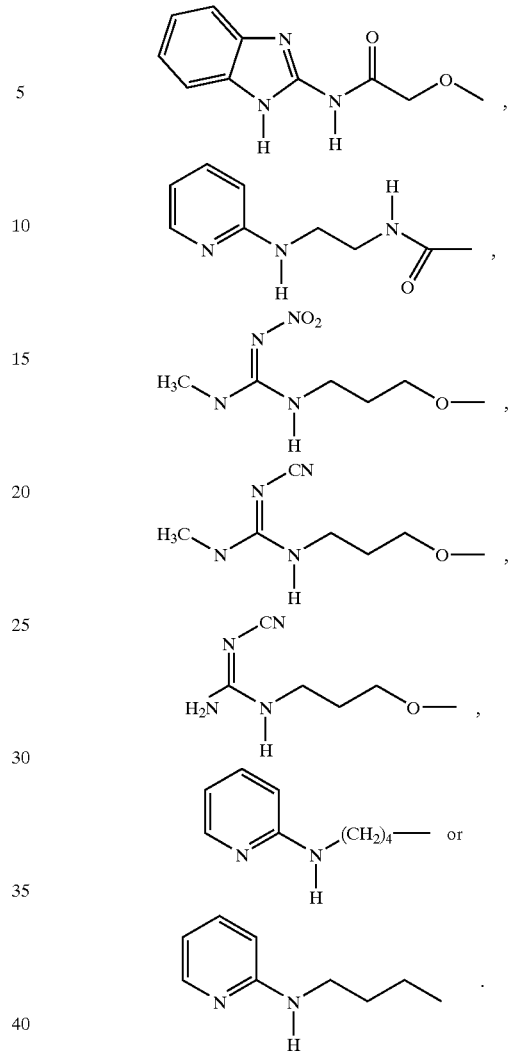

The substituent $R^3$—$(CH_2)_n$—A—$(CH_2)_m$—B— is preferably in the 5- or 6-position of the indole ring, particularly preferably in the 6-position.

Accordingly, the invention relates in particular to compounds of the formula I in which at least one of said radicals has one of the preferred meanings given above. Some preferred groups of compounds may be expressed by the following sub-formulae Ia to Ii, which correspond to the formula I and in which radicals not denoted in greater detail are as defined in the formula I, but in which In Ia X is a direct bond

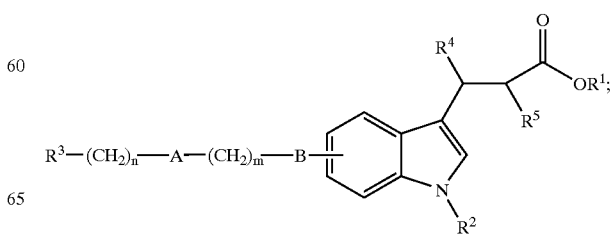

Ia

In Ib X is a direct bond,
R² is H,
R⁵ is H,
R⁴ is (CH₂)ₒ—Ar, and
o is 0

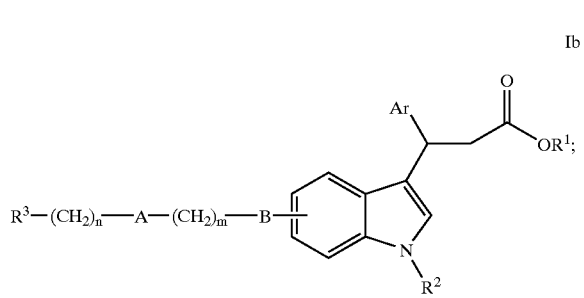
Ib

In Ic X is a direct bond,
R⁵ is H,
R⁴ is (CH₂)ₒ—Ar or Het, and
o is 0;
In Id X is a direct bond,
R⁵ is H,
B is O,
A is NH,
n is 0,
m is 3 or 4,
R³ is Het¹,
R⁴ is (CH₂)ₒ—Ar, and
o is 0

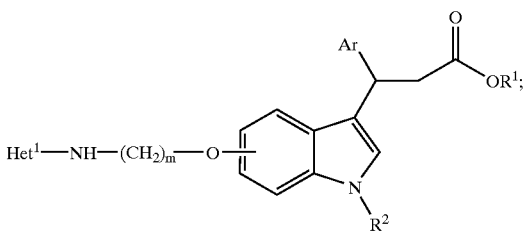
Id

In Ie X is a direct bond,
R⁵ is H,
B is O,
A is NH,
n is 0,
m is 3 or 4, and
R³ is Het¹

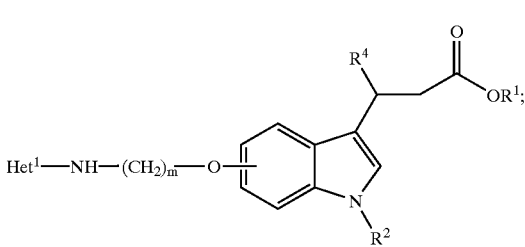
Ie

In If X is methylene which is unsubstituted or substituted by Ar,
R² is H,
R⁵ is H or Ar, and
R⁴ is oxo

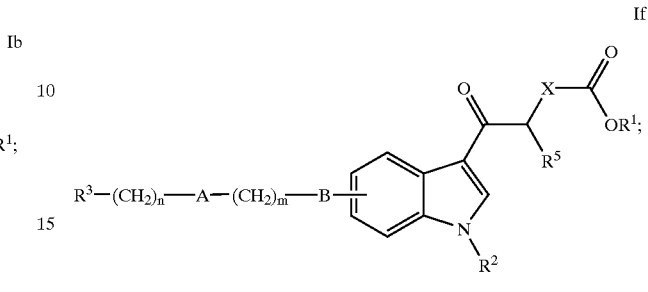
If

In Ig X is methylene,

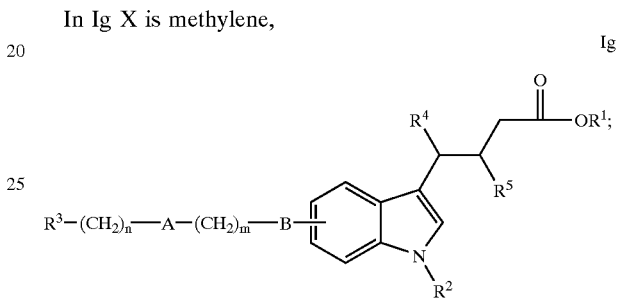
Ig

In Ih X is methylene,
R⁴ is H or (CH₂)ₒ—Ar,
R⁵ is H or (CH₂)ₒ—Ar,
o is 0, and
R² is H;
In Ii X is methylene,
R⁴ is H or (CH₂)ₒ—Ar,
R⁵ is H or (CH₂)ₒ—Ar,
o is 0,
B is O,
A is NH,
n is 0,
m is 3 or 4,
R³ is Het¹, and
R² is H

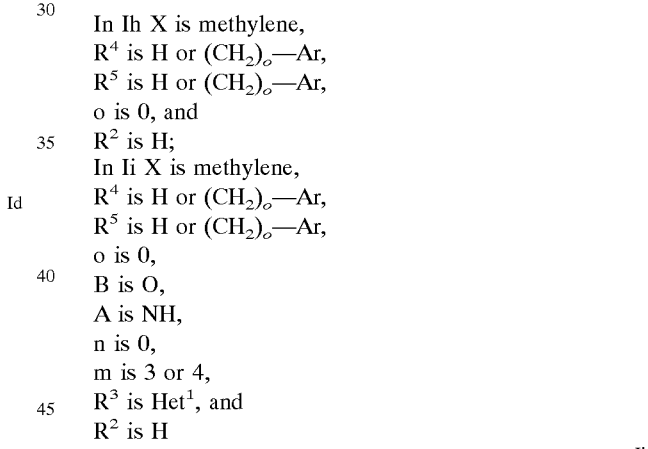
Ii

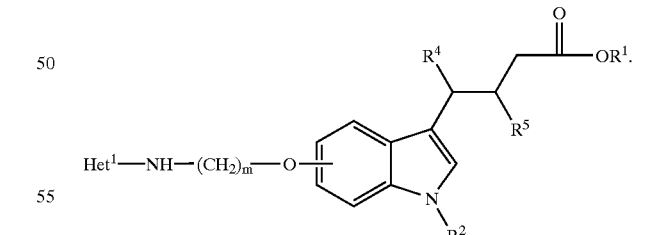

The compounds of the formula I according to claim 1 and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for said reactions. Use can also be made here of variants which are known per se, but are not mentioned here in greater detail.

If desired, the starting materials can also be formed in situ by not isolating them from the reaction mixture, but instead immediately converting them further into the compounds of the formula I according to claim 1.

Compounds of the formula I can preferably be obtained by liberating compounds of the formula I from one of their functional derivatives by treatment with a solvolyzing or hydrogenolyzing agent.

Preferred starting materials for the solvolysis or hydrogenolysis are those which conform to the formula I, but instead of one or more free amino and/or hydroxyl groups contain corresponding protected amino and/or hydroxyl groups, in particular those which instead of an H—N group carry an $SG^1$—N group, in which $SG^1$ is an amino protecting group, and/or those which instead of an H atom of a hydroxyl group carry a hydroxyl protecting group, for example those which conform to the formula I, but instead of a —COOH group carry a —COOSG² group, in which $SG^2$ is a hydroxyl protecting group.

It is also possible for a plurality of identical or different protected amino and/or hydroxyl groups to be present in the molecule of the starting material. If the protecting groups present are different from one another, they can in many cases be removed selectively (cf. in this respect: T. W. Greene, P. G. M. Wuts, *Protective Groups in Organic Chemistry*, $2^{nd}$ Edn., Wiley, New York 1991, or P. J. Kocienski, *Protecting Groups*, $1^{st}$ Edn., Georg Thieme Verlag, Stuttgart-New York, 1994, H. Kunz, H. Waldmann in *Comprehensive Organic Synthesis*, Vol. 6 (Eds. B. M. Trost, I. Fleming, E. Winterfeldt), Pergamon, Oxford, 1991, pp. 631–701).

The term "amino protecting group" is generally known and relates to groups which are suitable for protecting (blocking) an amino group against chemical reactions. Typical of such groups are, in particular, unsubstituted or substituted acyl, aryl, aralkoxymethyl or aralkyl groups. Since the amino protecting groups are removed after the desired reaction (or synthesis sequence), their type and size is furthermore not crucial; however, preference is given to those having 1–20 carbon atoms. The term "acyl group" is to be understood in the broadest sense in connection with the present process. It includes acyl groups derived aliphatic, araliphatic, alicyclic, aromatic and heterocyclic carboxylic acids and from sulfonic acids, as well as, in particular, alkoxycarbonyl, alkenyloxycarbonyl, aryloxy-carbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as phenoxyacetyl; alkoxycarbonyl, such as methoxycarbonyl, ethoxycarbonyl, 2,2,2-trichloroethoxycarbonyl, Boc and 2-iodoethoxycarbonyl; alkenyloxycarbonyl, such as allyloxycarbonyl (Aloc), aralkoxycarbonyl, such as CBZ (synonymous with Z), 4-methoxybenzyloxycarbonyl (MOZ), 4-nitrobenzyloxycarbonyl and 9-fluorenylmethoxycarbonyl (Fmoc); 2-(phenylsulfonyl)ethoxycarbonyl; trimethylsilylethoxycarbonyl (Teoc), and arylsulfonyl, such as 4-methoxy-2,3,6-trimethylphenylsulfonyl (Mtr). Preferred amino protecting groups are Boc, Fmoc and Aloc, furthermore Z, benzyl and acetyl.

The term "hydroxyl protecting group" is likewise generally known and relates to groups which are suitable for protecting a hydroxyl group against chemical reactions. Typical of such groups are the above-mentioned unsubstituted or substituted aryl, aralkyl, aroyl or acyl groups, furthermore also alkyl groups, alkyl-, aryl- and aralkylsilyl groups, and O, O- and O,S-acetals. The nature and size of the hydroxyl protecting groups is not crucial since they are removed again after the desired chemical reaction or synthesis sequence; preference is given to groups having 1–20 carbon atoms, in particular 1–10 carbon atoms. Examples of hydroxyl protecting groups are, inter alia, aralkyl groups, such as benzyl, 4-methoxybenzyl and 2,4-dimethoxybenzyl, aroyl groups, such as benzoyl and p-nitrobenzoyl, acyl groups, such as acetyl and pivaloyl, p-toluenesulfonyl, alkyl groups, such as methyl and tert-butyl, but also allyl, alkylsilyl groups, such as trimethylsilyl (TMS), triisopropylsilyl (TIPS), tert-butyldimethylsilyl (TBS) and triethylsilyl, trimethylsilylethyl, aralkylsilyl groups, such as tert-butyldiphenylsilyl (TBDPS), cyclic acetals, such as isopropylidene acetal, cyclopentylidene acetal, cyclohexylidene acetal, benzylidene acetal, p-methoxybenzylidene acetal and o,p-dimethoxybenzylidene acetal, acyclic acetals, such as tetrahydropyranyl (Thp), methoxymethyl (MOM), methoxyethoxymethyl (MEM), benzyloxymethyl (BOM) and methylthiomethyl (MTM). Particularly preferred hydroxyl protecting groups are benzyl, acetyl, tert-butyl and TBS.

The liberation of the compounds of the formula I from their functional derivatives is known from the literature for the protecting group used in each case (for example T. W. Greene, P. G. M. Wuts, *Protective Groups in Organic Chemistry*, $2^{nd}$ Edn., Wiley, New York 1991 or P.J. Kocienski, *Protecting Groups*, $1^{st}$ Edn., Georg Thieme Verlag, Stuttgart-New York, 1994). Use may also be made here of variants which are known per se, but are not mentioned here in greater detail.

Compounds of the formula I in which $R^3$=Het¹, B=O, A=NH and n=0 (formula I-1) can preferably be obtained in accordance with reaction scheme 1 below. $SG^3$ and $SG^4$ are hydroxyl protecting groups as defined above. $SG^5$ is an amino protecting group as described above. The radicals X, $R^1$, $R^2$, $R^4$ and $R^5$ and the variable m mentioned in the compounds I-1 and II–VI are as defined in claim 1.

Reaction scheme 1:

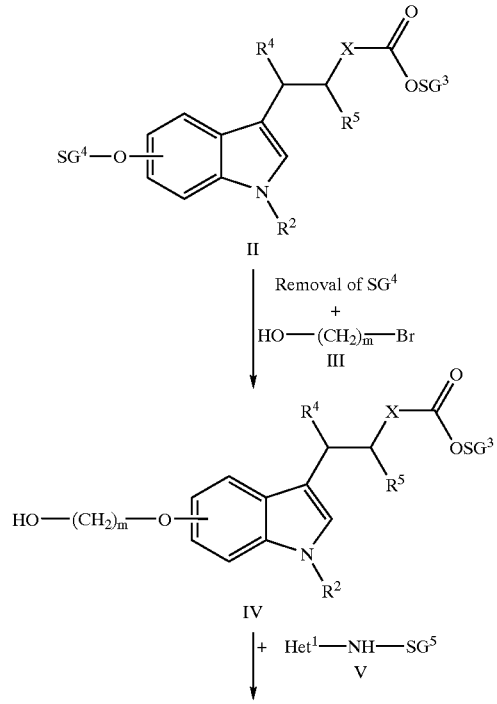

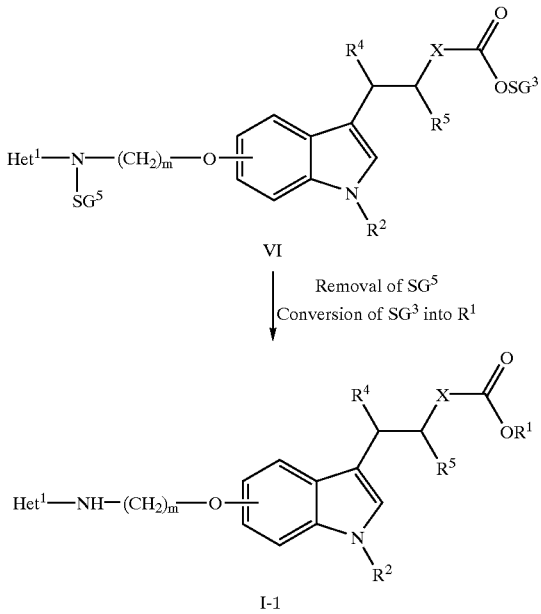

After removal of the hydroxyl protecting group $SG^4$ from the compound of the formula II under the corresponding known reaction conditions, a reaction is carried out with the compound of the formula III analogously to reaction conditions of nucleophilic substitutions. Under the known reaction conditions for a Mitsunobu reaction [literature: O. Mitsunobu, Synthesis 1981, 1–28], a reaction with a compound of the formula V is carried out in the subsequent step, and the amino protecting group $SG^5$ is correspondingly deblocked. Removal of the hydroxyl protecting group $SG^3$ gives a free acid of the formula I-1 ($R^1$=H). If desired, the hydroxyl protecting group $SG^3$ is converted into a substituent $R^1$.

The invention likewise relates to compounds of the formula IIa

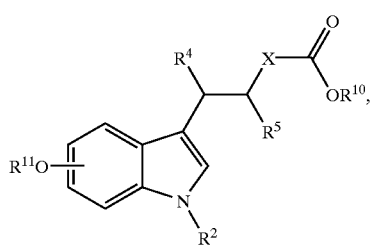

in which $R^2$, $R^4$ and $R^5$ are as defined in claim 1,

X is a bond, $R^{10}$ is a hydroxyl protecting group or H, and $R^{11}$ is a hydroxyl protecting group or H.

$R^{10}$ is preferably H or an alkyl group Z as hydroxyl protecting group, where Z is as defined above.

$R^{11}$ is preferably H or an aralkyl group as hydroxyl protecting group, as described above. The hydroxyl group $OR^{11}$ is preferably in the 6-position of the indole ring. Compounds of the formula IIa are valuable intermediates in the synthesis of the compounds of the formula I according to the invention in which X is a bond.

Preferred compounds of the formula IIa are ethyl 3-phenyl-3-(6-O-benzyl-indol-3-yl)propionate;
ethyl 3-phenyl-3-(6-hydroxy-indol-3-yl)propionate;
ethyl 3-phenyl-3-(5-O-benzyl-indol-3-yl)propionate;
ethyl 3-phenyl-3-(5-hydroxy-indol-3-yl)propionate;
ethyl 3-(4-methylphenyl)-3-(6-O-benzyl-indol-3-yl)propionate;
ethyl 3-(4-methylphenyl)-3-(6-hydroxy-indol-3-yl)propionate;
ethyl 3-(3-methylphenyl)-3-(6-O-benzyl-indol-3-yl)propionate;
ethyl 3-(3-methylphenyl)-3-(6-hydroxy-indol-3-yl)propionate;
ethyl 3-(2-methylphenyl)-3-(6-O-benzyl-indol-3-yl)propionate;
ethyl 3-(2-methylphenyl)-3-(6-hydroxy-indol-3-yl)propionate;
ethyl 3-[(4-trifluoromethyl)phenyl]-3-(6-O-benzylindol-3-yl)propionate;
ethyl 3-[(4-trifluoromethyl)phenyl]-3-(6-hydroxyindol-3-yl)propionate;
ethyl 3-(4-methoxyphenyl)-3-(6-O-benzylindol-3-yl)propionate;
ethyl 3-(4-methoxyphenyl)-3-(6-hydroxyindol-3-yl)propionate;
ethyl 3-(4-ethoxyphenyl)-3-(6-O-benzylindol-3-yl)propionate;
ethyl 3-(4-ethoxyphenyl)-3-(6-hydroxyindol-3-yl)propionate;
ethyl 3-(4-chlorophenyl)-3-(6-O-benzylindol-3-yl)propionate;
ethyl 3-(4-chlorophenyl)-3-(6-hydroxyindol-3-yl)propionate;
ethyl 3-(3-chlorophenyl)-3-(6-O-benzylindol-3-yl)propionate;
ethyl 3-(3-chlorophenyl)-3-(6-hydroxyindol-3-yl)propionate;
ethyl 3-(6-benzyloxy-1H-indol-3-yl)-3-pyridin-4-ylpropionate;
ethyl 3-(6-hydroxy-1H-indol-3-yl)-3-pyridin-4-ylpropionate;
ethyl 3-benzo-1,2,5-thiadiazol-4-yl-3-(6-benzyloxy-1H-indol-3-yl)propionate;
ethyl 3-benzo-1,2,5-thiadiazol-4-yl-3-(6-hydroxy-1H-indol-3-yl)propionate;
ethyl 3-benzo-1,2,5-thiadiazol-5-yl-3-(6-benzyloxy-1H-indol-3-yl)propionate;
ethyl 3-benzo-1,2,5-thiadiazol-5-yl-3-(6-hydroxy-1H-indol-3-yl)propionate;
ethyl 3-(6-benzyloxy-1H-indol-3-yl)-3-naphthalen-1-ylpropionate;
ethyl 3-(6-hydroxy-1H-indol-3-yl)-3-naphthalen-1-ylpropionate;
ethyl 3-(6-benzyloxy-1H-indol-3-yl)-3-naphthalen-2-ylpropionate;
ethyl 3-(6-hydroxy-1H-indol-3-yl)-3-naphthalen-2-ylpropionate;
ethyl 3-(6-benzyloxy-1H-indol-3-yl)-3-(1H-indol-2-yl)propionate;
ethyl 3-(6-hydroxy-1H-indol-3-yl)-3-(1H-indol-2-yl)propionate;
ethyl 3-(6-benzyloxy-1H-indol-3-yl)-3-(thiophen-2-yl)propionate;
ethyl 3-(6-hydroxy-1H-indol-3-yl)-3-(thiophen-2-yl)propionate;
ethyl 3-(6-benzyloxy-1H-indol-3-yl)-3-(1H-pyrrol-2-yl)propionate;

ethyl 3-(6-hydroxy-1H-indol-3-yl)-3-(1H-pyrrol-2-yl) propionate;
ethyl 3-(6-benzyloxy-1H-indol-3-yl)-3-(thiazol-2-yl) propionate;
ethyl 3-(6-hydroxy-1H-indol-3-yl)-3-(thiazol-2-yl) propionate;
ethyl 3-(6-benzyloxy-1H-indol-3-yl)-3-(1H-indol-2-yl) propionate;
ethyl 3-(6-hydroxy-1H-indol-3-yl)-3-(1H-indol-2-yl) propionate;
ethyl 3-biphenyl-4-yl-3-(6-benzyloxy-1H-indol-3-yl) propionate;
ethyl 3-biphenyl-4-yl-3-(6-hydroxy-1H-indol-3-yl) propionate;
ethyl 3-(3-cyano-4-dimethylamino-2-fluorophenyl)-3-(6-benzyloxy-1H-indol-3-yl)propionate;
ethyl 3-(3-cyano-4-dimethylamino-2-fluorophenyl)-3-(6-hydroxy-1H-indol-3-yl)propionate;
ethyl 3-(3-fluoro-4-trifluoromethylphenyl)-3-(6-benzyloxy-1H-indol-3-yl)-propionoate;
ethyl 3-(3-fluoro-4-trifluoromethylphenyl)-3-(6-hydroxy-1H-indol-3-yl)-propionate;
ethyl 3-(4-isopropylphenyl)-3-(6-benzyloxy-1H-indol-3-yl) propionate;
ethyl 3-(4-isopropylphenyl)-3-(6-hydroxy-1H-indol-3-yl) propionate;
ethyl 3-cyclohexyl-3-(6-benzyloxy-1H-indol-3-yl) propionate;
ethyl 3-cyclohexyl-3-(6-hydroxy-1H-indol-3-yl)propionate;
ethyl 3-cyclopropyl-3-(6-benzyloxy-1H-indol-3-yl) propionate;
ethyl 3-cyclopropyl-3-(6-hydroxy-1H-indol-3-yl) propionate;
ethyl 3-(6-benzyloxy-1H-indol-3-yl)-4,4-dimethyl-pentanoate;
ethyl 3-(6-hydroxy-1H-indol-3-yl)-4,4-dimethyl-pentanoate;
ethyl 3-(6-benzyloxy-1H-indol-3-yl)-5,5-dimethyl-hexanoate or
ethyl 3-(6-hydroxy-1H-indol-3-yl)-5,5-dimethyl-hexanoate.

Compounds of the formula IIa, as defined above, can be prepared analogously to Example 1 in accordance with reaction scheme 1a, where $R^5$ is H and $R^{11}$ is a hydroxyl protecting group $SG^4$.

Reaction scheme 1a:

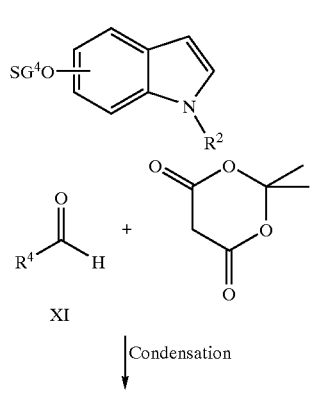

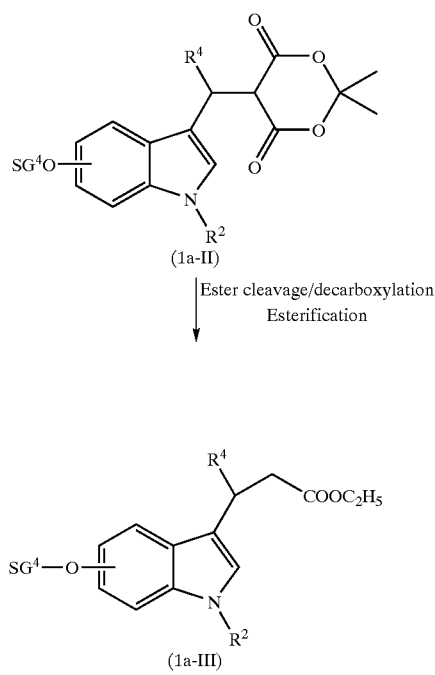

The condensation of a compound of the formula (1a-I) with an aldehyde XI and 2,2-dimethyl-1,3-dioxane-4,6-dione (Meldrum's acid) under reaction conditions known for condensation reactions gives compounds of the formula (1a-II). Combined ester cleavage/decarboxylation/esterification gives the ethyl ester of the formula (1a-III). The hydroxyl protecting group $SG^4$ can be removed by methods known from the literature, giving the free hydroxyl compounds of the formula IIa. Ester cleavage of the compounds of the formula (1a-II) or the hydroxyl analogues en gives the free acids of the formula IIa.

Compounds of the formula I in which $R^3$=Het$^1$, B=O, A=NHCO and n=0 (Formula I-2) can preferably be obtained in accordance with reaction scheme 2 below. $SG^3$, $SG^4$ and $SG^6$ are hydroxyl-protecting groups as defined above. The radicals X, $R^1$, $R^2$, $R^4$ and $R^5$ and the variable m mentioned in the compounds I-2, II and VII to IX are as defined in claim 1.

Reaction scheme 2:

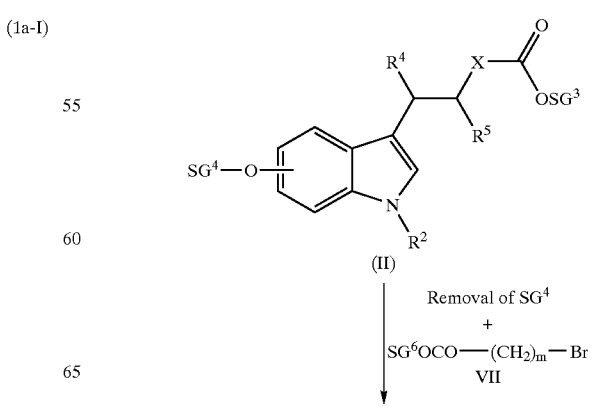

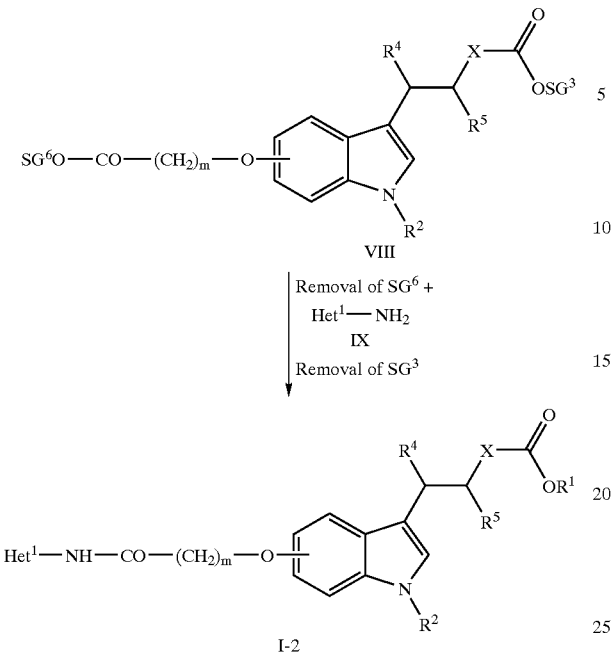

VIII

Removal of SG⁶ +
Het¹—NH₂
IX
Removal of SG³

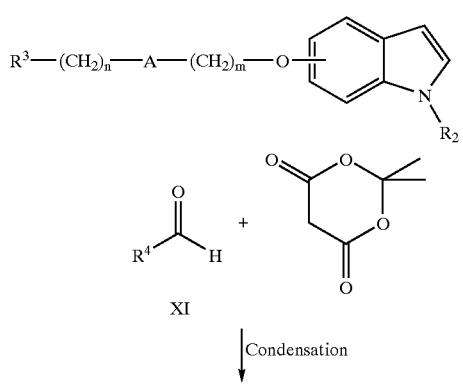

I-2

After removal of the hydroxyl protecting group $SG^4$ from the compound of the formula II under the corresponding known reaction conditions, a reaction is carried out with the compound of the formula VII analogously to reaction conditions of nucleophilic substitutions. After removal of the hydroxyl protecting group $SG^6$, a reaction with a compound of the formula IX is carried out under the known reaction conditions for peptide-analogous couplings. Removal of the hydroxyl protecting group $SG^3$ gives a free acid of the formula I-2 ($R^1$=H). If desired, the hydroxyl protecting group $SG^3$ is converted into a substituent $R^1$.

Compounds of the formula I in which B=O, X=a bond, $R^1$=H and $R^5$=H (formula I-3) can preferably be obtained in accordance with reaction scheme 3 below. The radicals $R^3$, $R^2$ and $R^4$ and the variables A, n and m mentioned in the compounds X–XII are as defined in claim 1, where free amino groups in $R^3$ are protected by amino protecting groups during the synthesis, and the protecting groups are removed in the final reaction step.

Reaction scheme 3:

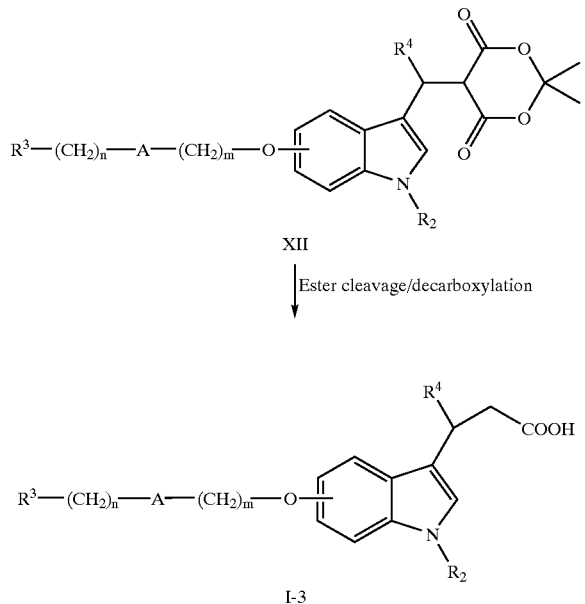

XII

Ester cleavage/decarboxylation

I-3

The condensation of a compound of the formula X with an aldehyde XI and 2,2-dimethyl-1,3-dioxane-4,6-dione under reaction conditions which are known for condensation reactions gives compounds of the formula XII. Ester cleavage and decarboxylation give the free acid of the formula I-3. If desired, the hydroxyl group is converted into a substituent $R^1$ or the acid of the formula I-3 is converted into a physiologically acceptable salt. Compounds of the formula X are obtained by alkylation of 1H-indol-6-ol using a bromide of the formula XIII ($R^3$—$(CH_2)_n$—A—$(CH_2)_m$—Br XIII), in which said radical $R^3$ and the variables A, n and m are as defined in claim 1.

Compounds of the formula I in which $R^3$=Het¹, $R^5$=H, X=a bond, A=NH, B=O and n=0 (formula I-4) can preferably be obtained in accordance with reaction scheme 4 below. In the compounds of the formula IIa, as described above, $R^{10}$ is $SG^3$ and $R^{11}$ is $SG^4$ (formula IIa-1), where $SG^3$ and $SG^4$ are hydroxyl protecting groups, as defined above. $SG^5$ is an amino protecting group as described above. The radicals $R^1$, $R^2$ and $R^4$ and the variable m mentioned in the compounds I-4 and XV–XVIII are as defined in claim 1.

Reaction scheme 4:

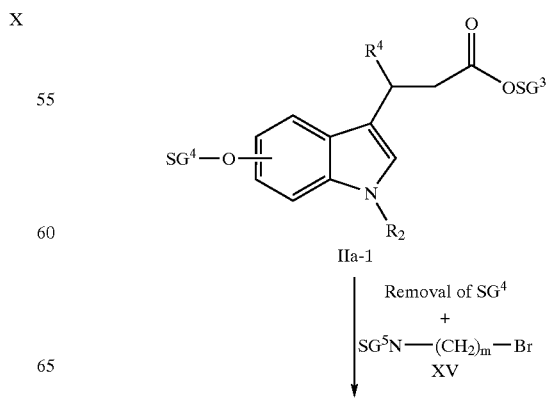

IIa-1

Removal of SG⁴
+
SG⁵N—(CH₂)ₘ—Br
XV

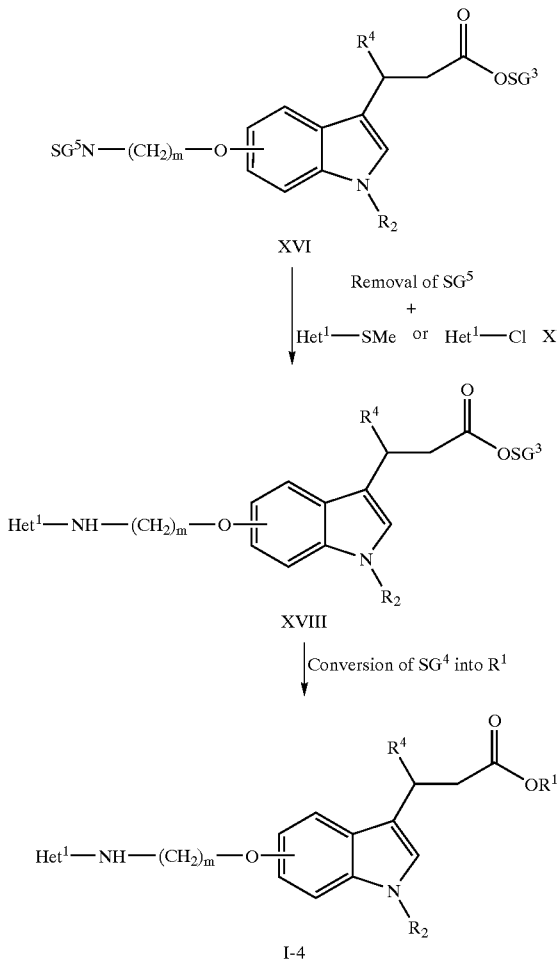

After removal of the hydroxyl protecting group SG⁴ from the compound of the formula IIa-1 in reaction scheme 4 under the corresponding known reaction conditions, a reaction is carried out with the compound of the formula XV analogously to reaction conditions of nucleophilic substitutions. In the subsequent step, the amino protecting group SG⁵ is removed, and the free amine is reacted with a thiomethyl or chloro compound of the formula XVII. Removal of the hydroxyl protecting group SG³ gives a free acid of the formula I-4 (R¹=H). If desired, the hydroxyl protecting group SG³ is converted into a substituent R¹.

Compounds of the formula I in which R³=—C(=NR⁶)—NHR⁶ or —C(=NR⁹)—NHR⁶, R⁵=H, X=a bond, A=NH, B=O and n=0 (formula I-5) can likewise preferably be obtained in accordance with reaction scheme 4.

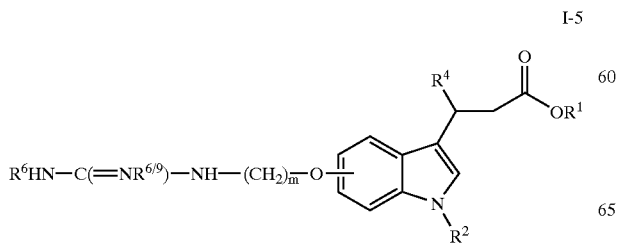

Instead of the reaction with compounds of the formula XVII (Het¹-SMe or Het¹-Cl), however, a reaction is carried out with a compound of the formula XIX

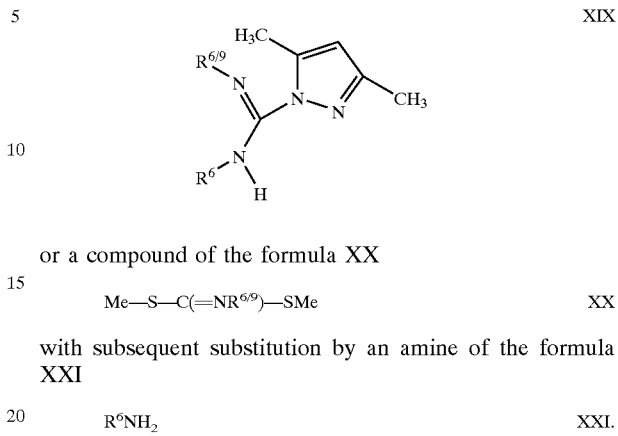

or a compound of the formula XX

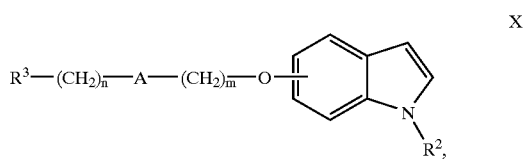

with subsequent substitution by an amine of the formula XXI

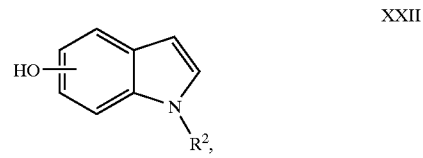

The radicals R⁶ and R⁹ mentioned in the compounds I-4 and XIX–XXI are as defined in claim 1.

Compounds of the formula X

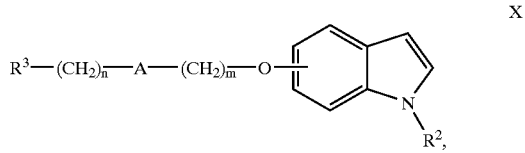

in which R², R³, A, n and m are as defined in claim 1, can be prepared analogously to the synthesis sequence in reaction scheme 4 by replacing the compound IIa-1 with a hydroxyl-substituted indole compound XXII

XXII

HO—[indole with N-R²]

in which R² is as defined in claim 1. After reaction of the hydroxyindole XXII with a compound of the formula XV and removal of the amino protecting group SG⁵, as described above, reaction is possible, depending on the substituent R³, with a compound of the formula XVII or XIX or with a compound of the formula XX followed by reaction with a compound of the formula XXI. Free amino groups in compounds of the formula XVII are protected by amino protecting groups during the synthesis.

The invention likewise relates to compounds of the formula X

X

R³—(CH₂)ₙ—A—(CH₂)ₘ—O—[indole with N-R²], in which
R², R³, A, n and m are as defined in claim 1, or salts thereof.

Preferred compounds of the formula X are 6-(3-(N-benzylpyridinium-2-yl-amino)propoxy)indole;
6-(3-(N-benzylpyridinium-2-yl-amino)propoxy)indole hydrobromide;
6-(3-(pyridin-2-yl-amino)propoxy)indole;
6-[3-(4,5-dihydro-1H-imidazol-2-yl-amino)propoxy]indole or
6-[3-(4,5-dihydro-1H-imidazol-2-yl-amino)butoxy]indole.

Examples of suitable inert solvents are hydrocarbons, such as hexane, petroleum ether, benzene, toluene and xylene; chlorinated hydrocarbons, such as trichloroethylene, 1,2-dichloroethane, tetrachloromethane, chloroform and dichloromethane; alcohols, such as methanol, ethanol, isopropanol, n-propanol, n-butanol and tert-butanol; ethers, such as diethyl ether, diisopropyl ether, tetrahydrofuran (THF) and dioxane; glycol ethers, such as ethylene glycol monomethyl and monoethyl ether, ethylene glycol dimethyl ether (diglyme); ketones, such as acetone and butanone; amides, such as acetamide, dimethylacetamide and dimethylformamide (DMF); nitriles, such as acetonitrile; sulfoxides, such as dimethylsulfoxide (DMSO); carbon disulfide; carboxylic acids, such as formic acid and acetic acid; nitro compounds, such as nitromethane and nitrobenzene; esters, such as ethyl acetate, and mixtures of said solvents.

It is furthermore possible for a radical $R^1$, $R^2$, $R^3$, $R^4$, $R^5$ and/or $R^6$ to be converted into another radical $R^1$, $R^2$, $R^3$, $R^4$, $R^5$ and/or $R^6$.

It is thus possible to saponify an ester of the formula I under standard conditions, for example NaOH in dioxane/water, 0–60° C.

The conversion of a cyano group into an amidino group is carried out by reaction with, for example, hydroxylamine followed by reduction of the N-hydroxyamidine using hydrogen in the presence of a catalyst, such as, for example, Pd/C.

In order to prepare an amidine of the formula I ($R^3$=—C(=NH)—$NH_2$), ammonia can be adducted onto a nitrile of the formula I. The adduction is preferably carried out in a number of steps by, in a manner known per se, a) converting the nitrile into a thioamide using $H_2S$ and then converting the thioamide into the corresponding S-alkylimidothioester using an alkylating agent, for example $CH_3I$, and then reacting the thioester with $NH_3$ to give the amidine, b) converting the nitrile into the corresponding imido ester using an alcohol, for example ethanol in the presence of HCl, and treating this ester with ammonia, or c) reacting the nitrile with lithium bis(trimethylsilyl)amide, and subsequently hydrolysing the product.

The conversion of an amino group into a guanidino group is carried out using an amidating agent, for example 1-amidino-3,5-dimethylpyrazole (DPFN), which is employed, in particular, in the form of its nitrate. The conversion is advantageously carried out with addition of a base, such as triethylamine or ethyl diisopropylamine, in an inert solvent or solvent mixture, for example water/dioxane, at temperatures of from 0 to 120° C., preferably from 60 to 120° C.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures of from −60 to +30° C.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I. On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

The compounds of the formula I contain at least one centre of chirality and can therefore exist in racemic or optically active form. Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture, for example in the volume ratio 82:15:3.

The diastereomer resolution can also be carried out by standard purification processes, such as, for example, chromatography or fractional crystallization.

It is of course also possible to obtain optically active compounds of the formula I by the methods described above by using starting materials which are already optically active.

The invention furthermore relates to pharmaceutical preparations comprising at least one compound of the formula I and/or a physiologically acceptable salt or solvate thereof prepared, in particular, by non-chemical methods. The compounds of the formula I can be brought into a suitable dosage form here together with at least one solid, liquid and/or semiliquid excipient or assistant and, if desired, in combination with one or more further active ingredients.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds can also be lyophilized and the resultant lyophilizates used, for example, for the preparation of injection preparations. The preparations indicated may be sterilized and/or comprise assistants, such as lubricants, preservatives, stabilizers and/or wetting agents, emulsifiers, salts for modifying the osmotic pressure, buffer substances, dyes, flavours and/or a plurality of further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

The compounds of the formula I and their physiologically acceptable salts can be used as integrin inhibitors in the combating of illnesses, in particular thromboses, cardiac infarction, coronary heart diseases, arteriosclerosis, tumours, osteoporosis, inflammations and infections.

The compounds of the formula I according to claim 1 and/or their physiologically acceptable salts are also used in pathological processes which are maintained or propagated by angiogenesis, in particular in tumours, restenoses, diabetic retinopathy, macular degenerative disease or rheumatoid arthritis.

The substances according to the invention are generally administered analogously to other known commercially available peptides, but in particular analogously to the compounds described in WO 99/30713 and WO 94/12478, preferably in doses of from about 0.05 to 500 mg, in particular from 0.5 to 100 mg, per dosage unit. The daily dose is preferably from about 0.01 to 2 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred.

Above and below, all temperatures are given in ° C. In the examples below, "conventional work-up" means that the organic phase is washed with saturated $NaHCO_3$ solution, if desired with water and saturated NaCl solution, the phases are separated, the organic phase is dried over sodium sulfate and evaporated, and the product is purified by chromatography on silica gel, by preparative HPLC and/or by crystallization. If desired, the purified compounds are freeze-dried.

HPLC: eluent A=water+0.3% of TFA, eluent B=acetonitrile/water+0.3% of TFA in the ratio 4:1. $R_t$ denotes the retention time. $R_f$ denotes the retention factor.

EXAMPLE 1

1. 5-[Phenyl(6-O-benzylindol-3-yl)methyl]-2,2-dimethyl-1,3-dioxane-4,6-dione 2

5 g (22.4 mmol) of 6-benzyloxyindole together with 2.26 ml (22.4 mmol) of benzaldehyde and 3.23 g (22.4 mmol) of Meldrum's acid (2,2-dimethyl-1,3-dioxane-4,6-dione) are dissolved in 100 ml of anhydrous acetonitrile and stirred at 30° C. in the presence of 129 mg (1.1 mmol) of L-proline until the reaction is complete (3 hours, TLC check). The mixture is allowed to cool to room temperature, and the precipitate formed is filtered off with suction and washed with ether. After thorough drying, the crude product 5-[phenyl(6-O-benzylindol-3-yl)methyl]-2,2-dimethyl-1,3-dioxane-4,6-dione is reacted further without further purification.

HPLC: (RP-18, gradient A/B 50:50→1:99 in 1 hour, where A=water+0.3% of TFA, B=acetonitrile/water+0.3% of TFA 4:1) $R_t$=41.4 min; TLC: Si-60, toluene/acetone 4:1, $R_f$=0.3; FAB-MS: (M+1)=456.

2. Ethyl 3-phenyl-3-(6-O-benzylindol-3-yl)propionate 3

5 g (11 mmol) of 2 are introduced into 30 ml of anhydrous pyridine together with 300 mg of copper powder and 3 ml of dried ethanol, and the mixture is refluxed with stirring for 3 hours (TLC check). The mixture is subsequently filtered through kieselguhr, the solution is evaporated, and the residue is taken up in ethyl acetate. Conventional work-up gives ethyl 3-phenyl-3-(6-O-benzylindol-3-yl)propionate, which is purified by chromatography on silica gel using toluene/acetone 20:1 as eluent.

HPLC: (RP-18, gradient A/B 50:50→1:99 in 1 hour as above) $R_t$=54 min; TLC: Si-60, toluene/acetone 4:1, $R_f$=0.7; FAB-MS: (M+1)=400.

3. Ethyl 3-phenyl-3-(6-hydroxyindol-3-yl)propionate 4

3.7 g (9.26 mmol) of 3 are dissolved in 60 ml of ethanol and hydrogenated for 2.5 hours at room temperature and atmospheric pressure in the presence of 900 mg of palladium/10% on activated carbon. When all the benzyl has been removed, the catalyst is filtered off and rinsed with a little ethanol, and the solution is evaporated, giving ethyl 3-phenyl-3-(6-hydroxyindol-3-yl)propionate.

HPLC: (RP-18, gradient A/B 99:1→1:99 in 1 hour) $R_t$=40.3 min; TLC: Si-60, toluene/acetone 4:1, $R_f$=0.2; FAB-MS: (M+1)=310.

4. Ethyl 3-phenyl-3-[6-(3-hydroxypropoxy)indol-3-yl] propionate 5

1.2 g (3.88 mmol) of 4 are refluxed overnight in 30 ml of acetone together with 0.66 ml (7.6 mmol) of 3-bromo-1-propanol and 2.1 g (15.2 mmol) of potassium carbonate. After cooling, the insoluble residue is filtered off, and the filtrate is evaporated. The crude product can be purified by chromatography on silica gel (eluent gradient toluene/acetone 9:1→4:1), giving ethyl 3-phenyl-3-[6-(3-hydroxypropoxy)indol-3-yl]propionate.

HPLC: (RP-18, gradient A/B 99:1→1:99 in 1 hour) $R_t$=42.4 min; TLC: Si-60, toluene/acetone 4:1, $R_f$=0.1; FAB-MS: (M+1)=368.

5. Ethyl 3-phenyl-3-(6-{3-[(pyridin-2-yl)(2,2,2-trichloroethoxycarbonyl)amino]propoxy}indol-3-yl) propionate 6

500 mg (1.36 mmol) of 5 and 550 mg (2.04 mmol) of 2-(2,2,2-trichloroethoxycarbonylamino)pyridine and 907 mg (2.72 mmol) of triphenylphosphine (polymer-bound) are introduced into 7.5 ml of anhydrous THF, and a solution of 0.32 ml (2.04 mmol) of azodicarboxylic acid diethyl ester (diethyl azodicarboxylate, DEAD) in 7.5 ml of THF is added dropwise at room temperature over the course of 30 minutes. The TLC check shows complete conversion after 1.5 hours.

The polymer is filtered off, and the solution is washed with a little water, dried and evaporated. The residue can be purified by chromatography on silica gel (eluent gradient toluene/acetone 20:1→4:1), giving ethyl 3-phenyl-3-(6-{3-[(pyridin-2-yl)(2,2,2-trichloroethoxycarbonyl)amino] propoxy}indol-3-yl)propionate.

HPLC: (RP-18, gradient A/B 99:1→1:99 in 1 hour) $R_t$=56.1 min

TLC: Si-60, toluene/acetone 4:1, $R_f$=0.5; FAB-MS: (M+1)=619.

6. Ethyl 3-phenyl-3-{6-[(3-pyridin-2-ylamino)propoxy]indol-3-yl}propionate 7

275 mg (0.44 mmol) of 6 are stirred for 2.5 hours at room temperature with 500 mg of zinc dust, 0.5 ml of water and 0.5 ml of acetic acid in 5 ml of THF. When the reaction is complete, the zinc is filtered off, the solution is evaporated, and the residue is purified by preparative HPLC on RP-18 (eluent gradient water/acetonitrile 99:1→1:99), giving ethyl 3-phenyl-3-{6-[(3-pyridin-2-ylamino)propoxy]indol-3-yl}propionate trifluoroacetate.

HPLC: (RP-18, gradient A/B 99:1→1:99 in 1 hour) $R_t$=42.8 min; FAB-MS: (M+1)=444.

7. 3-Phenyl-3-{6-[3-(pyridin-2-ylamino)propoxy]indol-3-yl}propionic acid 8

80 mg (0.18 mmol) of 7 are dissolved in 2 ml of dioxane, and the mixture is stirred overnight at room temperature with 0.9 ml of 1N NaOH (0.9 mmol). When the ether cleavage is complete, the solution is neutralized with a little acetic acid, giving 3-phenyl-3-{6-[3-(pyridin-2-ylamino)propoxy]indol-3-yl}-propionic acid. Preparative HPLC gives 3-phenyl-3-{6-[3-(pyridin-2-ylamino)propoxy]indol-3-yl}propionic acid trifluoroacetate; m.p. 232° (decomp.).

HPLC: (RP-18, gradient A/B 99:1→1:99 in 1 hour) $R_t$=34.7 min; FAB-MS: (M+1)=416.

EXAMPLE 2

1. Ethyl 3-phenyl-3-(6-{3-[(imidazol-2-yl)(2,2,2-trichloroethoxycarbonyl)amino]propoxy}indol-3-yl)propionate 9

Corresponding to Example 1.5, 907 mg (2.72 mmol) of triphenylphosphine (polymer-bound) are added to a solution of 500 mg (1.36 mmol) of 5, 527 mg (2.04 mmol) and 2-(2,2,2-trichloroethoxycarbonylamino)imidazole in 7.5 ml of anhydrous THF, and 0.32 ml (2.04 mmol) of DEAD are subsequently slowly added dropwise at room temperature. The solution is stirred over-night, the polymer is filtered off, and the THF solution is washed with water, dried over MgSO$_4$ and evaporated. The crude product is purified by preparative HPLC, giving ethyl 3-phenyl-3-(6-{3-[(imidazol-2-yl)(2,2,2-trichloroethoxycarbonyl)amino]propoxy}indol-3-yl)propionate trifluoroacetate.

HPLC: (RP-18, gradient A/B 99:1→1:99 in 1 hour) $R_t$=47.5 min; FAB-MS: (M+1)=608.

2. Ethyl 3-phenyl-3-{6-[3-(imidazol-2-ylamino)propoxy]indol-3-yl}propionate 10

Corresponding to Example 1.6, 185 mg (0.304 mmol) of 9 are reacted with 400 mg of zinc dust and 0.4 ml of acetic acid in 4 ml of THF, and the mixture is worked up. Purification is carried out by preparative HPLC on RP-18, giving ethyl 3-phenyl-3-{6-[3-(imidazol-2-ylamino)propoxy]indol-3-yl}propionate trifluoroacetate.

HPLC: (RP-18, gradient A/B 99:1→1:99 in 1 hour) $R_t$=40.9 min; FAB-MS: (M+1)=433.

3. 3-Phenyl-3-{6-[3-(imidazol-2-ylamino)propoxy]indol-3-yl}propionic acid 11

25 mg (0.058 mmol) of 10 are stirred at 70° C. for 36 hours in 1 ml of dioxane together with 0.3 ml of 1N HCl (0.3 mmol), giving 3-phenyl-3-{6-[3-(imidazol-2-ylamino) propoxy]indol-3-yl}propionic acid. Preparative HPLC gives 3-phenyl-3-{6-[3-(imidazol-2-ylamino)propoxy]indol-3-yl}propionic acid trifluoroacetate.

HPLC: (RP-18, gradient A/B 99:1→1:99 in 1 hour) $R_t$=33.4 min; FAB-MS: (M+1)=405.

EXAMPLE 3

Analogously to Example 1, Reaction of 6-benzyloxyindole with 4-methylbenzaldehyde and subsequent synthesis sequence gives 3-(4-methyl phenyl)-3-{6-[3-(pyridin-2-ylamino) propoxy]indol-3-yl}-propionic acid. After preparative HPLC: 3-(4-methylphenyl)-3-{6-[3-(pyridin-2-ylamino) propoxy]indol-3-yl}propionic acid trifluoroacetate;

with 3-methylbenzaldehyde and subsequent synthesis sequence gives 3-(3-methyl phenyl)-3-{6-[3-(pyridin-2-ylamino) propoxy]indol-3-yl}-propionic acid. After preparative HPLC: 3-(3-methylphenyl)-3-{6-[3-(pyridin-2-ylamino) propoxy]indol-3-yl}propionic acid trifluoroacetate;

with 2-methylbenzaldehyde and subsequent synthesis sequence gives 3-(2-methylphenyl)-3-{6-[3-(pyridin-2-ylamino)propoxy] indol-3-yl}-propionic acid. After preparative HPLC: 3-(2-methylphenyl)-3-{6-[3-(pyridin-2-ylamino)propoxy]indol-3-yl}propionic acid trifluoroacetate;

with 4-trifluoromethylbenzaldehyde and subsequent synthesis sequence gives 3-(4-trifluoromethylphenyl)-3-{6-[3-(pyridin-2-ylamino) propoxy]indol-3-yl}propionic acid. After preparative HPLC: 3-(4-trifluoromethylphenyl)-3-{6-[3-(pyridin-2-ylamino)propoxy]indol-3-yl}propionic acid trifluoroacetate;

with 4-methoxybenzaldehyde and subsequent synthesis sequence gives 3-(4-methoxyphenyl)-3-{6-[3-(pyridin-2-ylamino) propoxy]indol-3-yl}-propionic acid. After preparative HPLC: 3-(4-methoxyphenyl)-3-{6-[3-(pyridin-2-ylamino) propoxy]indol-3-yl}propionic acid trifluoroacetate;

with 4-ethoxybenzaldehyde and subsequent synthesis sequence gives 3-(4-ethoxyphenyl)-3-{6-[3-(pyridin-2-ylamino) propoxy]indol-3-yl}-propionic acid. After preparative HPLC: 3-(4-ethoxyphenyl)-3-{6-[3-(pyridin-2-ylamino) propoxy]indol-3-yl}propionic acid trifluoroacetate;

with 4-chlorobenzaldehyde and subsequent synthesis sequence gives 3-(4-chlorophenyl)-3-{6-[3-(pyridin-2-ylamino)propoxy] indol-3-yl}-propionic acid. After preparative HPLC: 3-(4-chlorophenyl)-3-{6-[3-(pyridin-2-ylamino)propoxy]indol-3-yl}propionic acid trifluoroacetate;

with 3-chlorobenzaldehyde and subsequent synthesis sequence gives 3-(3-chlorophenyl)-3-{6-[3-(pyridin-2-ylamino)propoxy] indol-3-yl}-propionic acid. After preparative HPLC: 3-(3-chlorophenyl)-3-{6-[3-(pyridin-2-ylamino)propoxy]indol-3-yl}propionic acid trifluoroacetate;

HPLC: (RP-18, gradient A/B 99:1→1:99 in 1 hour) $R_t$=34.3 min; FAB-MS: (M+1)=450 with pyridine-4-carbaldehyde and subsequent synthesis sequence gives 3-pyridin-4-yl-3-{6-[3-(pyridin-2-ylamino)propoxy]-1H-indol-3-yl}-propionic acid. After preparative HPLC: 3-pyridin-4-yl-3-{6-[3-(pyridin-2-ylamino)propoxy]-1H-indol-3-yl}propionic acid trifluoroacetate;

HPLC: (RP-18, gradient A/B 99:1→1:99 in 1 hour) $R_t$=20.7 min; FAB-MS: (M+1)=417 with benzo-1,2,5-thiadiazole-4-carbaldehyde and subsequent synthesis sequence gives 3-benzo-1,2,5-thiadiazole-4-yl-3-{6-[3-(pyridin-2-ylamino)propoxy]-1H-indol-3-yl}propionic acid. After preparative HPLC: 3-benzo-1,2,5-thiadiazole-4-yl-3-{6-[3-(pyridin-2-ylamino)propoxy]-1H-indol-3-yl}propionic acid trifluoroacetate;
with naphthalene-1-carbaldehyde and subsequent synthesis sequence gives
3-naphthalene-1-yl-3-{6-[3-(pyridin-2-ylamino)propoxy]-1H-indol-3-yl}-propionic acid. After preparative HPLC: 3-naphthalen-1-yl-3-{6-[3-(pyridin-2-ylamino)propoxy]-1H-indol-3-yl}propionic acid trifluoroacetate or
with naphthalene-2-carbaldehyde and subsequent synthesis sequence gives
3-naphthalene-2-yl-3-{6-[3-(pyridin-2-ylamino)propoxy]-1H-indol-3-yl}-propionic acid. After preparative HPLC: 3-naphthalen-2-yl-3-{6-[3-(pyridin-2-ylamino)propoxy]-1H-indol-3-yl}propionic acid trifluoroacetate.

EXAMPLE 4

Analogously to Example 2, Reaction of 6-benzyloxyindole with 4-methylbenzaldehyde and subsequent synthesis sequence gives
3-(4-methylphenyl)-3-{6-[3-(imidazol-2-ylamino)propoxy]indol-3-yl}-propionic acid. After preparative HPLC: 3-(4-methylphenyl)-3-{6-[3-(imidazol-2-ylamino)propoxy]indol-3-yl}propionic acid trifluoroacetate;
with 3-methylbenzaldehyde and subsequent synthesis sequence gives
3-(3-methyl phenyl)-3-{6-[3-(imidazol-2-ylamino)propoxy]indol-3-yl}-propionic acid. After preparative HPLC: 3-(3-methylphenyl)-3-{6-[3-(imidazol-2-ylamino)propoxy]indol-3-yl}propionic acid trifluoroacetate;
with 2-methylbenzaldehyde and subsequent synthesis sequence gives
3-(2-methylphenyl)-3-{6-[3-(imidazol-2-ylamino)propoxy]indol-3-yl}-propionic acid. After preparative HPLC: 3-(2-methylphenyl)-3-{6-[3-(imidazol-2-ylamino)propoxy]indol-3-yl}propionic acid trifluoroacetate;
with 4-trifluoromethylbenzaldehyde and subsequent synthesis sequence gives
3-(4-trifluoromethylphenyl)-3-{6-[3-(imidazol-2-ylamino)propoxy]indol-3-yl}propionic acid. After preparative HPLC: 3-(4-trifluoromethylphenyl)-3-{6-[3-(imidazol-2-ylamino)propoxy]indol-3-yl}propionic acid trifluoroacetate;
with 4-methoxybenzaldehyde and subsequent synthesis sequence gives
3-(4-methoxyphenyl)-3-{6-[3-(imidazol-2-ylamino)propoxy]indol-3-yl}-propionic acid. After preparative HPLC: 3-(4-methoxyphenyl)-3-{6-[3-(imidazol-2-ylamino)propoxy]indol-3-yl}propionic acid trifluoroacetate;
with 4-ethoxybenzaldehyde and subsequent synthesis sequence gives
3-(4-ethoxyphenyl)-3-{6-[3-(imidazol-2-ylamino)propoxy]indol-3-yl}-propionic acid. After preparative HPLC: 3-(4-ethoxyphenyl)-3-{6-[3-(imidazol-2-ylamino)propoxy]indol-3-yl}propionic acid trifluoroacetate;
with 4-chlorobenzaldehyde and subsequent synthesis sequence gives
3-(4-chlorophenyl)-3-{6-[3-(imidazol-2-ylamino)propoxy]indol-3-yl}-propionic acid. After preparative HPLC: 3-(4-chlorophenyl)-3-{6-[3-(imidazol-2-ylamino)propoxy]indol-3-yl}propionic acid trifluoroacetate;
with 4-fluorobenzaldehyde and subsequent synthesis sequence gives
3-(4-fluorophenyl)-3-{6-[3-(imidazol-2-ylamino)propoxy]indol-3-yl}-propionic acid. After preparative HPLC: 3-(4-fluorophenyl)-3-{6-[3-(imidazol-2-ylamino)propoxy]indol-3-yl}propionic acid trifluoroacetate;
with pyridine-4-carbaldehyde and subsequent synthesis sequence gives
3-pyridin-4-yl-3-{6-[3-(imidazol-2-ylamino)propoxy]-1H-indol-3-yl}-propionic acid. After preparative HPLC: 3-pyridin-4-yl-3-{6-[3-(imidazol-2-ylamino)propoxy]-1H-indol-3-yl}propionic acid trifluoroacetate;
with benzo-1,2,5-thiadiazole-4-carbaldehyde and subsequent synthesis sequence gives
3-benzo-1,2,5-thiadiazole-4-yl-3-{6-[3-(imidazol-2-ylamino)propoxy]-1H-indol-3-yl}propionic acid. After preparative HPLC: 3-benzo-1,2,5-thiadiazole-4-yl-3-{6-[3-(imidazol-2-ylamino)propoxy]-1H-indol-3-yl}-propionic acid trifluoroacetate;
with naphthalene-1-carbaldehyde and subsequent synthesis sequence gives
3-naphthalene-1-yl-3-{6-[3-(imidazol-2-ylamino)propoxy]-1H-indol-3-yl}-propionic acid. After preparative HPLC: 3-naphthalen-1-yl-3-{6-[3-(imidazol-2-ylamino)propoxy]-1H-indol-3-yl}propionic acid trifluoroacetate or
with naphthalene-2-carbaldehyde and subsequent synthesis sequence gives
3-naphthalene-2-yl-3-{6-[3-(imidazol-2-ylamino)propoxy]-1H-indol-3-yl}-propionic acid. After preparative HPLC: 3-naphthalen-2-yl-3-{6-[3-(imidazol-2-ylamino)propoxy]-1H-indol-3-yl}propionic acid trifluoroacetate.

EXAMPLE 5

1. Ethyl 3-phenyl-3-[6-(4-hydroxybutoxy)indol-3-yl]propionate 12

Analogously to Example 1.4, 1.2 g (3.88 mmol) of ethyl 3-phenyl-3-(6-hydroxyindol-3-yl)propionate are reacted with 1.16 g (7.6 mmol) of 4-bromo-1-butanol in the presence of 2.1 g (15.2 mmol) of potassium carbonate in 30 ml of acetone, giving ethyl 3-phenyl-3-[6-(4-hydroxybutoxy)indol-3-yl]propionate.

HPLC: (RP-18, gradient A/B 99:1→1:99 in 1 hour as above) $R_t$=43.4 min; TLC: Si-60, toluene/acetone 4:1, $R_f$=0.13; FAB-MS: (M+1)=382.

2. Ethyl 3-phenyl-3-(6-{4-[(pyridin-2-yl)(2,2,2-trichloroethoxycarbonyl)amino]butoxy}indol-3-yl)propionate 13

The reaction of 170 mg (0.45 mmol) of 12 with 178 mg (0.66 mmol) of 2-(2,2,2-trichloroethoxycarbonylamino)pyridine in the presence of 293 mg (0.88 mmol) of triphenylphosphine (polymer-bound) and 0.103 ml (0.66 mmol) of DEAD in 6 ml of THF in accordance with Example 1.5 gives, after work-up and chromatography, ethyl 3-phenyl-3-(6-{4-[(pyridin-2-yl)(2,2,2-trichloroethoxycarbonyl)amino]butoxy}indol-3-yl)propionate.

HPLC: (RP-18, gradient A/B 99:1→1:99 in 1 hour as above) $R_t$=57.4 min; TLC: Si-60, toluene/acetone 4:1, $R_f$=0.47; FAB-MS: (M+1)=633.

3. Ethyl 3-phenyl-3-{6-[4-(pyridin-2-ylamino)butoxy]indol-3-yl}propionate 14

Analogously to Example 1.6, removal of Troc using zinc in acetic acid/THF gives ethyl 3-phenyl-3-{6-[4-(pyridin-2-ylamino)butoxy]indol-3-yl}propionate.

HPLC: (RP-18, gradient A/B 99:1→1:99 in 1 hour as above) $R_t$=44.3 min; FAB-MS: (M+1)=458.

4. 3-Phenyl-3-{6-[4-(pyridin-2-ylamino)butoxy]indol-3-yl}propionic acid 15

Analogously to Example 1.7, ethyl ester cleavage under basic conditions using 1 N sodium hydroxide solution in dioxane gives 3-phenyl-3-{6-[4-(pyridin-2-ylamino)butoxy]indol-3-yl}propionic acid. Preparative HPLC gives 3-phenyl-3-{6-[4-(pyridin-2-ylamino)butoxy]indol-3-yl}propionic acid trifluoroacetate.

HPLC: (RP-18, gradient A/B 99:1→1:99 in 1 hour as above) $R_t$=36.1 min. FAB-MS: (M+1)=430.

EXAMPLE 6

1. Analogously to Example 1, reaction of 5-benzyloxyindole with benzaldehyde and Meldrum's acid and subsequent synthesis sequence gives 3-phenyl-3-{5-[3-(pyridin-2-ylamino)propoxy]indol-3-yl}propionic acid. After preparative HPLC: 3-phenyl-3-{5-[3-(pyridin-2-ylamino)propoxy]indol-3-yl}-propionic acid trifluoroacetate, m.p. 240° (decomp.).

HPLC: (RP-18, gradient A/B 99:1→1:99 in 1 hour as above) $R_t$=33.5 min; FAB-MS: (M+1)=416.

2. Analogously to Example 1, reaction of 5-benzyloxyindole with benzaldehyde and Meldrum's acid and subsequent synthesis sequence with 4-bromo-1-butanol gives 3-phenyl-3-{5-[4-(pyridin-2-ylamino)butoxy]indol-3-yl}propionic acid. After preparative HPLC: 3-phenyl-3-{5-[4-(pyridin-2-yl-amino)butoxy]indol-3-yl}propionic acid trifluoroacetate.

HPLC: (RP-18, gradient A/B 99:1→1:99 in 1 hour as above) $R_t$=35.1 min; FAB-MS: (M+1)=430.

EXAMPLE 7

1. Ethyl 3-phenyl-3-[6-(tert-butoxycarbonylmethoxy)indol-3-yl]propionate 18

The compound ethyl 3-phenyl-3-(6-hydroxyindol-3-yl)propionate 4 prepared analogously to Example 1.1–1.3 (3.23 mmol) is stirred overnight at 60° C. with 0.94 ml (6.4 mmol) of tert-butyl bromoacetate and 1.8 g (13 mmol) of potassium carbonate in 20 ml of acetone. When the reaction is complete (TLC check toluene/acetone 4:1), the residue is filtered off, the solution is evaporated, and the crude product is purified by chromatography on silica gel (eluent toluene/acetone 9:1), giving ethyl 3-phenyl-3-[6-(tert-butoxycarbonylmethoxy)indol-3-yl]propionate.

TLC: Si-60, toluene/acetone 4:1, $R_f$=0.56; FAB-MS: (M+1)=424.

2. Ethyl 3-phenyl-3-(6-carboxymethoxyindol-3-yl)propionate 19

1 g (2.36 mmol) of 18 are dissolved in 20 ml of dichloromethane and stirred at room temperature for 20 hours with 2 ml of trifluoroacetic acid. The solution is subsequently evaporated, and the residue is purified by preparative HPLC on RP-18, giving ethyl 3-phenyl-3-(6-carboxymethoxyindol-3-yl)-propionate trifluoroacetate.

HPLC: (RP-18, gradient A/B 99:1→1:99 in 1 hour) $R_t$=40.72 min; FAB-MS: (M+1)=368.

3. Ethyl 3-phenyl-3-[6-(pyridin-2-ylamidocarboxymethoxy)indol-3-yl]-propionate 20

100 mg (0.27 mmol) of 19 are stirred overnight at room temperature with 51 mg (0.54 mmol) of 2-aminopyridine in the presence of 112 mg (0.35 mmol) of TBTU (O-(benzotriazol-1-yl)-N,N,N',N'-tetramethyluronium tetrafluoroborate), 11 mg (81 μmol) of HOBT (1-hydroxybenzotriazole hydrate) and 90 μl (0.82 mmol) of 4-methylmorpholine in 5 ml of DMF. When the reaction is complete, the reaction solution is poured into 100 ml of water and extracted with ethyl acetate. Conventional work-up gives ethyl 3-phenyl-3-[6-(pyridin-2-ylamidocarboxymethoxy)indol-3-yl]propionate.

HPLC: (RP-18, gradient A/B 99:1→1:99 in 1 hour) $R_t$=40.96 min; FAB-MS: (M+1)=444.

4. 3-Phenyl-3-[6-(pyridin-2-ylamidocarboxymethoxy)indol-3-yl]propionic acid 21

The reaction of 50 mg (113 μmol) of 20 with 0.15 ml of 1N NaOH in 1 ml of dioxane at room temperature gives, after 24 hours, 3-phenyl-3-[6-(pyridin-2-ylamidocarboxymethoxy)indol-3-yl]propionic acid. After preparative HPLC: 3-phenyl-3-[6-(pyridin-2-ylamidocarboxymethoxy)indol-3-yl]-propionic acid trifluoroacetate.

HPLC: (RP-18, gradient A/B 99:1→1:99 in 1 hour) $R_t$=32.1 min; FAB-MS: (M+1)=416.

EXAMPLE 8

1. Analogously to Example 7.3, ethyl 3-phenyl-3-(6-carboxymethoxyindol-3-yl)propionate is reacted with 2-aminoimidazole. Ester saponification under the conditions of Example 7.4 gives 3-phenyl-3-[6-(benzimidazol-2-yl-amidocarboxymethoxy)indol-3-yl]propionic acid. After preparative HPLC: 3-phenyl-3-[6-(benzimidazol-2-ylamidocarboxymethoxy)indol-3-yl]propionic acid trifluoroacetate.

HPLC: (RP-18, gradient A/B 99:1→1:99 in 1 hour) $R_t$=35.4 min; FAB-MS: (M+1)=455.

1. Analogously to Example 7.3, ethyl 3-phenyl-3-(6-carboxymethoxyindol-3-yl)propionate is reacted with 2-aminobenzimidazole. Ester saponification under the conditions of Example 7.4 gives 3-phenyl-3-[6-(imidazol-2-yl-amidocarboxymethoxy)indol-3-yl]propionic acid. After preparative HPLC: 3-phenyl-3-[6-(imidazol-2-ylamidocarboxymethoxy)indol-3-yl]propionic acid trifluoroacetate.

HPLC: (RP-18, gradient A/B 99:1→1:99 in 1 hour) $R_t$=29.3 min FAB-MS: (M+1)=405.

EXAMPLE 9

1. 6-(3-benzyloxycarbonylaminopropoxy)indole 22

10 g (75 mmol) of 6-hydroxyindole and 21.5 g (79 mmol) of 3-benzyloxycarbonylaminopropyl bromide are dissolved in 150 ml of acetonitrile and stirred at 80° C. for 12 hours with 31.1 g (225 mmol) of potassium carbonate. When the reaction is complete (TLC check: silica gel Si-60 with toluene/acetone 10:1), the insoluble residue is filtered off, the solution is evaporated, and the product is purified by chromatography on silica gel using toluene/acetone 10:1 as eluent.

HPLC/MS: (Chromolith RP-18, gradient A:B from 80:20→0:100 in 3.5 min using A=water+0.01% of TFA, B=acetonitrile) $R_t$=2.13 min; TLC: Si-60, toluene/acetone 6:1, $R_f$=0.31; FAB-MS: (M+1)=325.

2. 6-(3-Aminopropoxy)indole 23

15 g (46 mmol) of 22 are dissolved in 100 ml of ethanol and hydrogenated at room temperature (RT) under atmospheric pressure using 2 g of palladium/activated carbon (10%). After 4 hours, the catalyst is filtered off and the solution is evaporated. The crude product can be used for the next reactions without further purification.

HPLC: (RP-18, gradient A:B from 99:1→1:99 in 1 hour) $R_t$=19.1 min;

TLC: Si-60, ethyl acetate/methanol/water 4:3:2, $R_f$=0.07; FAB-MS: (M+1)=191.

3. 6-(3-(N-benzylpyridinium-2-ylamino)propoxy)indole hydrobromide 24 3.5 g (18.4 mmol) of 23 are stirred for 12 hours at RT under a protective gas (nitrogen) with 5.2 g (18.4 mmol) of N-benzyl-2-chloropyridinium hydrobromide in the presence of 11 g (129 mmol) of sodium hydrogencarbonate in 200 ml of ethanol. When the reaction is complete, the inorganic salts are filtered off, and the solution is evaporated under reduced pressure.

HPLC: (RP-18, gradient A:B from 99:1→1:99 in 1 hour) $R_t$=35.6 min; TLC: Si-60, dichloromethane/methanol 6:1, $R_f$=0.55; FAB-MS: M$^+$=438.

4. 3-[(1-(4-fluorophenyl)-2-(4,6-dioxo-2,2-dimethyl-1,3-dioxan-5-yl)ethyl]-6-[3-(N-benzyl pyridinium-2-ylamino)propoxy]indole Hydrobromide 25

500 mg (1.05 mmol) of 24 are stirred for 12 hours at 30° C. with 110 μl (1.05 mmol) of 4-fluorobenzaldehyde, 150 mg (1.05 mmol) of Meldrum's acid (2,2-dimethyl-1,3-dioxane-4,6-dione) and 6 mg (0.05 mmol) of L-proline in 4 ml of acetonitrile. After the solution has been evaporated, the crude product is triturated with MTB ether (methyl tert-butyl ether), and the crystalline residue is filtered off with suction. This can be further used directly for ester cleavage and decarboxylation.

HPLC-MS: (Chromolith RP-18, gradient A:B from 80:20→0:100 in 3.5 min, where A=water+0.01% of TFA, B=acetonitrile), $R_t$=1.77 min; M⁺=608.

5. 3-(4-Fluorophenyl)-3-{6-[3-(N-benzylpyridinium-2-ylamino)propoxy]indol-3-yl}propionic acid trifluoroacetate 26

295 mg (0.43 mmol) of 25 are dissolved in 3.5 ml of DMSO and stirred for 12 hours at 100° C. with 36 mg (0.85 mmol) of lithium chloride and 9 µl of water. When the reaction is complete (HPLC/MS check), the solution is evaporated, and the residue is purified by preparative HPLC on RP-18. After the HPLC solution has been freeze-dried, the product is obtained as a white, amorphous solid in the form of the trifluoroacetate.

HPLC: (RP-18, gradient A:B from 99:1→1:99 in 1 hour) $R_t$=38.1 min; FAB-MS: (M⁺)=524.

6. 3-(4-fluorophenyl)-3-{6-[3-(pyridin-2-ylamino)propoxy]indol-3-yl}propionic acid 27

60 mg (94 µmol) of 26 are dissolved in 5 ml of acetone and hydrogenated for 10 hours at RT and atmospheric pressure in the presence of 40 mg (0.48 mmol) of sodium hydrogen carbonate and 20 mg of palladium/activated carbon (10%). Removal of the catalyst by filtration and evaporation of the solution gives 3-(4-fluorophenyl)-3-{6-[3-(pyridin-2-ylamino)propoxy]indol-3-yl}propionic acid. Preparative HPLC on RP-18 gives 3-(4-fluorophenyl)-3-{6-[3-(pyridin-2-ylamino)propoxy]indol-3-yl}propionic acid trifluoroacetate.

HPLC: (RP-18, gradient A:B from 99:1→1:99 in 1 hour) $R_t$=31.6 min; FAB-MS: (M+1)=434.

EXAMPLE 10

Analogously to Example 9, the Reaction of 6-(3-(N-benzylpyridinium-2-yl-amino)propoxy)indole Hydrobromide 24
with 3,5-bis(trifluoromethyl)benzaldehyde and subsequent synthesis sequence gives
3-[3,5-bis(trifluoromethyl)phenyl]-3-{6-[3-(pyridin-2-ylamino)propoxy]-indol-3-yl}propionic acid. After preparative HPLC: 3-[3,5-bis(trifluoromethyl)phenyl]-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=36.5 min; FAB-MS: (M+1)=594.
with 3,5-dichlorobenzaldehyde and subsequent synthesis sequence gives
3-(3,5-dichlorophenyl)-3-{6-[3-(pyridin-2-ylamino)propoxy]indol-3-yl}-propionic acid. After preparative HPLC: 3-(3,5-dichlorophenyl)-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=37.2 min; FAB-MS: (M+1)=485.
with 4,6-dichlorobenzaldehyde and subsequent synthesis sequence gives
3-(4,6-dichlorophenyl)-3-{6-[3-(pyridin-2-ylamino)propoxy]indol-3-yl}-propionic acid. After preparative HPLC: 3-(4,6-dichlorophenyl)-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=37.3 min; FAB-MS: (M+1)=485.
with 4-chloro-5-trifluoromethylbenzaldehyde and subsequent synthesis sequence gives
3-(4-chloro-5-trifluoromethyl phenyl)-3-{6-[3-(pyridin-2-ylamino)propoxy]-indol-3-yl}propionic acid. After preparative HPLC: 3-(4-chloro-5-trifluoromethyl phenyl)-3-{6-[3-(pyridin-2-ylamino)propoxy]indol-3-yl}-propionic acid trifluoroacetate;
HPLC: (RP-18, gradient A:B from 99:1→1:99 in 1 hour) $R_t$=38.7 min; FAB-MS: (M+1)=518.
with 3-cyclohexylbenzaldehyde and subsequent synthesis sequence gives
3-cyclohexyl-3-{6-[3-(pyridin-2-ylamino)propoxy]indol-3-yl}propionic acid. After preparative HPLC: 3-cyclohexyl-3-{6-[3-(pyridin-2-yl-amino)propoxy]indol-3-yl}propionic acid trifluoroacetate;
HPLC: (RP-18, gradient A:B from 99:1→1:99 in 1 hour) $R_t$=37.2 min; FAB-MS: (M+1)=422.
with benzo-1,2,5-thiadiazole-5-carbaldehyde and subsequent synthesis sequence gives
3-benzo-1,2,5-thiadiazol-5-yl-3-{6-[3-(pyridin-2-ylamino)propoxy]-1H-indol-3-yl}propionic acid. After preparative HPLC: 3-benzo-1,2,5-thiadiazol-5-yl -3-{6-[3-(pyridin-2-ylamino)propoxy]-1H-indol-3-yl}propionic acid trifluoroacetate;
HPLC: (RP-18, gradient A:B from 99:1→1:99 in 1 hour) $R_t$=30.7 min; FAB-MS: (M+1)=474.
with 2,6-difluorobenzaldehyde and subsequent synthesis sequence gives
3-(2,6-difluorophenyl)-3-{6-[3-(pyridin-2-ylamino)propoxy]indol-3-yl}-propionic acid. After preparative HPLC: 3-(2,6-difluorophenyl)-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=32.6 min; FAB-MS: (M+1)=452.
with 2-chloro-3,6-difluorobenzaldehyde and subsequent synthesis sequence gives
3-(2-chloro-3,6-difluorophenyl)-3-{6-[3-(pyridin-2-ylamino)propoxy]indol-3-yl}propionic acid. After preparative HPLC: 3-(2-chloro-3,6-difluorophenyl)-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=34.6 min; FAB-MS: (M+1)=486.
with 2,4,6-trifluorobenzaldehyde and subsequent synthesis sequence gives
3-(2,4,6-trifluorophenyl)-3-{6-[3-(pyridin-2-ylamino)propoxy]indol-3-yl}-propionic acid. After preparative HPLC: 3-(2,4,6-trifluorophenyl)-3-{6-[3-(pyridin-2-ylamino)propoxy]indol-3-yl}propionic acid trifluoroacetate;
HPLC: (RP-18, gradient A:B from 99:1→1:99 in 1 hour) $R_t$=33.8 min; FAB-MS: (M+1)=470.
with 4-methoxycarbonylbenzaldehyde and subsequent synthesis sequence gives
3-(4-methoxycarbonyl phenyl)-3-{6-[3-(pyridin-2-ylamino)propoxy]indol-3-yl}propionic acid. After preparative HPLC: 3-(4-methoxycarbonylphenyl)-3-{6-[3-(pyridin-2-ylamino)propoxy]indol-3-yl}propionic acid trifluoroacetate.

EXAMPLE 11

1. 6-[3-(Pyridin-2-ylamino)propoxy]indole 28

6 g (12.9 mmol) of 6-(3-(N-benzylpyridinium-2-ylamino)propoxy)indole hydrobromide 24 (prepared analogously to Example 9.1–9.3] are dissolved in 300 ml of acetone and hydrogenated for 8 hours at RT and atmospheric pressure in the presence of 2 g of palladium/activated carbon (10%). After the catalyst has been filtered off, the solution is evaporated, and the crude product is obtained as a white solid.

TLC: Si-60, dichloromethane/methanol 6:1, $R_f$=0.67; HPLC: (RP-18, gradient A:B from 99:1→1:99 in 1 hour) $R_t$=28.6 min; FAB-MS: (M+1)=268.

2. 3-[(1-(4-trifluoromethoxyphenyl)-2-(4,6-dioxo-2,2-dimethyl-1,3-dioxan-5-yl)ethyl]-6-[3-(pyridin-2-ylamino)propoxy]indole 29

350 mg (1.3 mmol) of 28 are stirred for 12 hours at RT with 190 µl (1.3 mmol) of 4-trifluoromethoxybenzaldehyde, 190 mg (1.3 mmol) of Meldrum's acid and 9 mg (0.07 mmol) of proline in 5 ml of acetonitrile. When the reaction is complete (check by HPLC/MS), the solution is evaporated, and the product is employed for ester cleavage and decarboxylation without further purification.

HPLC/MS: (Chromolith RP-18, gradient A:B from 80:20→0:100 in 3.5 min, where A=water+0.01% of TFA, B=acetonitrile), $R_t$=1.71 min; (M+1)=544.

3. 3-(4-Trifluoromethoxyphenyl)-3-{6-[3-(pyridin-2-ylamino)propoxy]-indol-3-yl}propionic acid trifluoroacetate 30

Corresponding to Example 9.5, 760 mg (1.3 mmol) of 29 are stirred for 12 hours at 100° C. in 4 ml of DMSO with 110 mg of lithium chloride and 29 µl of water. When the reaction is complete, the solution is evaporated, giving 3-(4-Trifluoromethoxyphenyl)-3-{6-[3-(pyridin-2-ylamino)propoxy]indol-3-yl}propionic acid. Preparative HPLC on RP-18 gives 3-(4-trifluoromethoxyphenyl)-3-{6-[3-(pyridin-2-ylamino)propoxy]indol-3-yl}propionic acid trifluoroacetate.

HPLC: (RP-18, gradient A:B from 99:1→1:99 in 1 hour) $R_t$=:36.7 min; FAB-MS: (M+1)=498.

Analogously to Example 11, the reaction of 6-[3-(pyridin-2-ylamino)propoxy]indole 28 with 3-trifluoromethoxybenzaldehyde and subsequent synthesis sequence gives 3-(3-trifluoromethoxyphenyl)-3-{6-[3-(pyridin-2-ylamino)propoxy]indol-3-yl}propionic acid. Preparative HPLC gives 3-(3-trifluoromethoxyphenyl)-3-{6-[3-(pyridin-2-ylamino)propoxy]indol-3-yl}propionic acid trifluoroacetate;

HPLC: (RP-18, gradient A:B from 99:1→1:99 in 1 hour) $R_t$=40.2 min; FAB-MS: (M+1)=500

EXAMPLE 12

1. 6-[3-(4,5-dihydro-1H-imidazol-2-ylamino)propoxy]indole 31

500 mg (2.6 mmol) of 6-(3-aminopropoxy)indole 23 [prepared in accordance with Example 9.1] are dissolved in 10 ml of DMF together with 0.97 g (3.9 mmol) of 2-(3,5-dimethylpyrazolyl)-4,5-dihydroimidazole hydrobromide and 1.7 ml (11.9 mmol) of triethylamine, and the solution is stirred at 60° C. for 12 hours. After the solution has been evaporated, the crude product is purified by preparative HPLC.

HPLC: (RP-18, gradient A:B from 99:1→1:99 in 1 hour) $R_t$=26.7 min; FAB-MS: (M+1)=259.

2. 3-[(1-(Benzo-1,2,5-thiadiazol-5-yl)-2-(4,6-dioxo-2,2-dimethyl-1,3-dioxan-5-yl)ethyl]-6-[3-(4,5-dihydro-1H-imidazol-2-ylamino)propoxy]indole 32

In accordance with Example 11.2, 100 mg (0.33 mmol) of 31 are reacted with 53 mg (0.33 mmol) of 5-formylbenzo-1,2,5-thiadiazole, 46 mg (0.33 mmol) of Meldrum's acid and 2 mg of L-proline in 4 ml of acetonitrile at 30° C. Evaporation gives a residue which is further reacted without purification.

HPLC/MS: (Chromolith RP-18, gradient A:B from 80:20→0:100 in 3.5 min, where A=water+0.01% of TFA, B=acetonitrile) $R_t$=1.29 min; (M+1)=549.

2. 3-(Benzo-1,2,5-thiadiazol-5-yl)-3-{6-[3-(4,5-dihydro-1H-imidazol-2-ylamino)propoxy]indol-3-yl}propionic acid 33

The crude product 32 is stirred for 12 hours at 100° C. in 4 ml of DMSO together with 27 mg of lithium chloride and 7 µl of water, and then evaporated, giving 3-(benzo-1,2,5-thiadiazol-5-yl)-3-{6-[3-(4,5-dihydro-1H-imidazol-2-ylamino)propoxy]indol-3-yl}propionic acid. Purification by preparative HPLC gives 3-(benzo-1,2,5-thiadiazol-5-yl)-3-{6-[3-(4,5-dihydro-1H-imidazol-2-ylamino)propoxy]indol-3-yl}propionic acid trifluoroacetate.

HPLC: (RP-18, gradient A:B from 99:1→1:99 in 1 hour) $R_t$=28.1 min; FAB-MS: (M+1)=465.

EXAMPLE 13

Analogously to Example 12, the Reaction of 6-[3-(4,5-dihydro-1H-imidazol-2-ylamino)propoxy]indole 31 with 4-fluorobenzaldehyde and subsequent synthesis sequence gives 3-{6-[3-(4,5-dihydro-1H-imidazol-2-ylamino)propoxy]-1H-indol-3-yl}-3-(4-fluorophenyl)propionic acid. Preparative HPLC gives 3-{6-[3-(4,5-dihydro-1H-imidazol-2-ylamino)propoxy]-1H-indol-3-yl}-3-(4-fluorophenyl)propionic acid trifluoroacetate;

with benzaldehyde and subsequent synthesis sequence gives

3-{6-[3-(4,5-dihydro-1H-imidazol-2-ylamino)propoxy]-1H-indol-3-yl}-3-phenylpropionic acid. Preparative HPLC gives 3-{6-[3-(4,5-dihydro-1H-imidazol-2-ylamino)propoxy]-1H-indol-3-yl}-3-phenylpropionic acid trifluoroacetate;

HPLC: (RP-18, gradient A:B from 99:1→1:99 in 1 hour) $R_t$=29.8 min; FAB-MS: (M+1)=407.

with pyridine-4-carbaldehyde and subsequent synthesis sequence gives 3-pyridin-4-yl-3-{6-[3-(4,5-dihydro-1H-imidazol-2-ylamino)propoxy]-1H-indol-3-yl}propionic acid. Preparative HPLC gives 3-pyridin-4-yl-3-{6-[3-(3,5-dihydro-1H-imidazol-2-ylamino)propoxy]-1H-indol-3-yl}propionic acid trifluoroacetate.

Analogously to Example 12, the reaction of 6-[3-(4,5-dihydro-1H-imidazol-2-ylamino)butoxy]indole, prepared analogously to Example 9.1–9.3 by reaction with 4-benzyloxycarbonylaminobutyl bromide, with benzaldehyde and subsequent synthesis sequence gives 3-{6-[4-(4,5-dihydro-1H-imidazol-2-ylamino)butoxy]-1H-indol-3-yl}-3-phenylpropionic acid. Preparative HPLC gives 3-{6-[4-(4,5-dihydro-1H-imidazol-2-ylamino)butoxy]-1H-indol-3-yl}-3-phenylpropionic acid trifluoroacetate;

HPLC: (RP-18, gradient A:B from 99:1→1:99 in 1 hour) $R_t$=30.5 min; FAB-MS: (M+1)=421.

EXAMPLE 14

1. Ethyl 3-phenyl-3-[6-(3-phthalimidopropoxy)indol-3-yl]propionate 34

25 g (81 mmol) of ethyl 3-phenyl-3-(6-hydroxyindol-3-yl)propionate 4 [prepared in accordance with Example 1.1–1.2] are dissolved in 250 ml of acetonitrile together with 30.3 g (113 mmol) of N-(3-bromopropyl)phthalimide, 26.4 g (80.6 mmol) of caesium carbonate and 0.67 g (4 mmol) of potassium iodide are added, and the mixture is refluxed for 12 hours. The reaction mixture is allowed to cool and is then filtered through a layer of kieselguhr, and the filtrate is evaporated. The crude product can be recrystallized from hot ethanol.

m.p.: 95° C., TLC: Si-60, toluene/MTB ether 4:1, $R_f$=0.31, HPLC: (RP-18, gradient A:B from 99:1→1:99 in 1 hour) $R_t$=49.9 min, FAB-MS: (M+1)=497.

2. Ethyl 3-phenyl-3-[6-(3-aminopropoxy)indol-3-yl]propionate Hydrochloride 35

34.6 g (69.7 mmol) of 34 are dissolved in 350 ml of ethanol and refluxed with 5.1 ml (104.5 mmol) of hydrazine hydrate until the reaction is complete after 2.5 hours. After the solution has been cooled in an ice bath, the precipitated phthalohydrazide is filtered off, and the solution is acidified using ethanolic HCl. The new precipitate of the phthalohydrazide hydrochloride is again filtered off with suction, and the solution is concentrated to about 100 ml. The product crystallizes from the ethanolic solution at 0° C. as the hydrochloride.

m.p.: 158° C., TLC: Si-60, dichloromethane/methanol/ ammonia 4:1:0.1, $R_f$=0.33; FAB-MS: (M+1)=367.

3. 3-Phenyl-3-[6-(3-aminopropoxy)indol-3-yl]propionic acid 36 1.6 g (4 mmol) of 35 are dissolved in 10 ml of dioxane and stirred for 2 days at RT with 10 ml of 2N sodium hydroxide solution. When the reaction is complete, the solution is neutralized using 2N HCl, and the product is precipitated in acetone. The compound can be reacted further without purification.

HPLC: (RP-18, gradient A:B from 99:1→1:99 in 1 hour) $R_t$=25.8 min; FAB-MS: (M+1)=339.

4. 3-Phenyl-3-[6-(3-guanidinopropoxy)indol-3-yl]propionic acid 37 250 mg (0.74 mmol) of 36 are stirred for 12 hours at 60° C. with 223 mg (1.11 mmol) of 3,5-dimethyl-1-pyrazoloylformamidinium nitrate and 0.31 ml (2.22 mmol) of triethylamine in 10 ml of DMF. When the reaction is complete (HPLC/MS check), the solution is evaporated, giving 3-phenyl-3-[6-(3-guanidinopropoxy)indol-3-yl] propionic acid. Purification by preparative HPLC gives 3-phenyl-3-[6-(3-guanidinopropoxy)indol-3-yl]propionic acid trifluoroacetate.

HPLC: (RP-18, gradient A:B from 99:1→1:99 in 1 hour) $R_t$=28.9 min; FAB-MS: (M+1)=381.

EXAMPLE 15

Analogously to Example 14, the reaction of ethyl 3-phenyl-3-(6-hydroxyindol-3-yl)propionate 4 with N-(4-bromobutyl)phthalimide and subsequent synthesis sequence gives 3-[6-(4-guanidinobutoxy)-1H-indol-3-yl]-3-phenylpropionic acid. Preparative HPLC gives 3-[6-(4-guanidinobutoxy)-1H-indol-3-yl]-3-phenylpropionic acid trifluoroacetate, HPLC: (RP-18, gradient A:B from 99:1→1:99 in 1 hour) $R_t$=30.6 min; FAB-MS: (M+1)=395.

EXAMPLE 16

3-Phenyl-3-{6-[3-(1,5-dihydroimidazol-4-on-2-ylamino) propoxy]indol-3-yl}propionic acid 38

130 mg (0.29 mmol) of 36, prepared analogously to Example 14, are stirred for 24 hours at RT with 115 mg (0.87 mmol) of 2-methylsulfanyl-1,5-dihydroimidazol-4-one and 0.12 ml (0.87 mmol) of triethylamine in a mixture of 2 ml of ethanol and 1 ml of DMF, giving 3-phenyl-3-{6-[3-(1,5-dihydroimidazol-4-on-2-ylamino)propoxy]indol-3-yl}propionic acid. Purification by preparative HPLC on RP-18 gives 3-phenyl-3-{6-[3-(1,5-dihydroimidazol-4-on-2-ylamino)propoxy]indol-3-yl}propionic acid trifluoroacetate.

FAB-MS: (M+1)=421.

EXAMPLE 17

Analogously to Example 16, the reaction of 3-(4-fluorophenyl)-3-[6-(3-aminopropoxy)indol-3-yl]propionic acid (prepared analogously to Example 1.1–1.2 and 15) with 2-methylsulfanyl-1,5-dihydroimidazol-4-one and subsequent synthesis sequence gives 3-(4-fluorophenyl)-3-{6-[3-(4-oxo-4,5-dihydro-1H-imidazol-2-ylamino)propoxy]-1H-indol-3-yl}propionic acid. Preparative HPLC gives 3-(4-fluorophenyl)-3-{6-[3-(4-oxo-4,5-dihydro-1H-imidazol-2-ylamino)propoxy]-1H-indol-3-yl}propionic acid trifluoroacetate.

Analogously to Example 16, the reaction of 3-[6-(3-aminopropoxy)-1H-indol-3-yl]-3-pyridin-4-ylpropionic acid (prepared analogously to Example 1.1–1.2 and 15) with 2-methylsulfanyl-1,5-dihydroimidazol-4-one and subsequent synthesis sequence gives 3-{6-[3-(4-oxo-4,5-dihydro-1H-imidazol-2-ylamino) propoxy]-1H-indol-3-yl}-3-pyridin-4-ylpropionic acid. Preparative HPLC gives 3-{6-[3-(4-oxo-4,5-dihydro-1H-imidazol-2-ylamino)propoxy]-1H-indol-3-yl}-3-pyridin-4-yl-propionic acid trifluoroacetate.

Analogously to Example 16, the reaction of 3-[6-(3-aminopropoxy)-1H-indol-3-yl]-3-benzo-1,2,5-thiadiazol-5-ylpropionic acid (prepared analogously to Example 1.1–1.2 and 15) with 2-methylsulfanyl-1,5-dihydroimidazol-4-one and subsequent synthesis sequence gives 3-benzo-1,2,5-thiadiazol-5-yl-3-{6-[3-(4-oxo-4,5-dihydro-1H-imidazol-2-ylamino)propoxy]-1H-indol-3-yl}propionic acid. Preparative HPLC gives 3-benzo-1,2,5-thiadiazol-5-yl-3-{6-[3-(4-oxo-4,5-dihydro-1H-imidazol-2-yl-amino)propoxy]-1H-indol-3-yl}propionic acid trifluoroacetate.

EXAMPLE 18

Ethyl 3-phenyl-3-{6-[3-(pyrimidin-2-ylamino)propoxy] indol-3-yl}propionate 39

1 g (2.48 mmol) of 35, prepared in accordance with Example 14.2, are dissolved in 30 ml of anhydrous ethanol together with 426 mg (3.72 mmol) of 2-chloropyrimidine and 1 ml (7.44 mmol) of triethylamine, and the solution is refluxed for 20 hours. After evaporation, the residue is chromatographed on silica gel (eluent ethyl acetate).

TLC: Si-60, ethyl acetate, $R_f$=0.42; HPLC: (RP-18, gradient A:B from 99:1→1:99 in 1 hour) $R_t$=39.0 min; FAB-MS: (M+1)=445.

Ester cleavage using sodium hydroxide solution in dioxane at RT gives the free acid 3-phenyl-3-{6-[3-(pyrimidin-2-ylamino)propoxy]indol-3-yl}propionic acid.

FAB-MS: (M+1)=417.

EXAMPLE 19

Ethyl 3-phenyl-3-{6-[3-(3,4,5,6-tetrahydropyrimidin-2-ylamino)propoxy]-indol-3-yl}propionate 40

200 mg (0.45 mmol) of 39 are dissolved in 10 ml of ethanol and hydrogenated for 3 hours at RT and atmospheric pressure in the presence of 0.68 ml (1.35 mmol) of 2N HCl and 60 mg of palladium/activated carbon (10%). When the reaction is complete, the catalyst is filtered off, the solution is evaporated, and the residue is purified by preparative HPLC on RP-18.

TLC: Si-60, ethyl acetate/methanol 4:1, $R_f$=0.08; HPLC/MS: (Chromolith RP-18, gradient A:B from 80:20→0:100 in 3.5 min, where A=water+0.01% of TFA, B=acetonitrile) $R_t$=1.39 min; FAB-MS: (M+1)=449.

Ether cleavage of the ethyl ester using sodium hydroxide in dioxane at RT gives the free acid 3-phenyl-3-{6-[3-(3,4,5,6-tetrahydropyrimidin-2-yl-amino)propoxy]indol-3-yl}propionic acid.

FAB-MS: M+1=421.

EXAMPLE 20

1. Ethyl 3-phenyl-3-{6-[3-(3,4,5,6-tetrahydropyridin-2-yl) aminopropoxy]-indol-3-yl}propionate 41

In accordance with Example 19, 200 mg of ethyl 3-phenyl-3-{6-[3-(pyridin-2-ylamino)propoxy]indol-3-yl}propionate 7 are hydrogenated in the presence of 2N hydrochloric acid and palladium/activated carbon (10%) to give 41.

FAB-MS: (M+1)=448.

Ester cleavage using sodium hydroxide solution in dioxane at RT gives the free acid 3-phenyl-3-{6-[3-(3,4,5,6-tetrahydropyridin-2-yl)aminopropoxy]-indol-3-yl}propionic acid.

FAB-MS: (M+1)=420.

2. Analogously to Example 9, compound 24 is reacted with 3-hydroxybenzaldehyde and subsequent synthesis sequence to give methyl 3-(3-hydroxyphenyl)-3-{6-[3-(pyridin-2-ylamino)propoxy]-1H-indol-3-yl}-propionate.

Analogously to Example 19, methyl 3-(3-hydroxyphenyl)-3-{6-[3-(pyridin-2-ylamino)propoxy]-1H-indol-3-yl}propionate is hydrogenated, giving methyl 3-(3-hydroxyphenyl)-3-{6-[3-(3,4,5,6-tetrahydropyridin-2-ylamino)propoxy]-1H-indol-3-yl}propionate.

Ester cleavage using sodium hydroxide solution in dioxane at RT gives the free acid 3-(3-hydroxyphenyl)-3-{6-[3-(3,4,5,6-tetrahydropyridin-2-ylamino)propoxy]-1H-indol-3-yl}propionic acid.

HPLC: (RP-18, gradient A:B from 99:1→1:99 in 1 hour) $R_t$=26.6 min; FAB-MS: (M+1)=436.

EXAMPLE 21

1. 3-Phenyl-3-{6-[3-(thiomethyl-N-cyanoiminomethyl) aminopropoxy]indol-3-yl}propionic acid 42

1 g (2.9 mmol) of 36 are stirred for 20 hours at 80° C. with 1.3 g (8.7 mmol) of dimethyl N-cyanodithioiminocarbonate in 10 ml of DMF. When the reaction is complete, the solution is evaporated, and the crude product 42 is purified by chromatography on silica gel using toluene/ethyl acetate 1:1 as eluent.

TLC: Si-60, toluene/methanol 3:1, $R_f$=0.55; HPLC/MS: (Chromolith RP-18, gradient A:B from 80:20→0:100 in 3.5 min, where A=water+0.01% of TFA, B=acetonitrile) $R_t$=1.75 min; M+1=437.

2. Phenyl-3-{6-[3-(N'-methyl-N''-cyanoguanidino)propoxy] indol-3-yl}-propionic acid 43

100 mg (0.23 mmol) of 42 are dissolved in 2 ml of DMF, and the solution is stirred for 12 hours at 60° C. with 1 ml of methylamine solution (33% in ethanol). The solution is subsequently evaporated, giving phenyl-3-{6-[3-(N'-methyl-N''-cyanoguanidino)propoxy]indol-3-yl}propionic acid. Purification by preparative HPLC on RP-18 gives phenyl-3-{6-[3-(N'-methyl-N''-cyanoguanidino)propoxy] indol-3-yl}propionic acid trifluoroacetate.

TLC: Si-60, dichloromethane/methanol 1:1, $R_f$=0.53; HPLC/MS: (Chromolith RP-18, gradient A:B from 80:20→0:100 in 3.5 min, where A=water+0.01% of TFA, B=acetonitrile) $R_t$=1.49 min; M+1=420.

EXAMPLE 22

Analogously to Example 1, the Reaction of 6-benzyloxyindole with 1H-indole-2-carbaldehyde and subsequent synthesis sequence gives 3-(1H-indol-2-yl)-3-{6-[3-(pyridin-2-ylamino)propoxy]-1H-indol-3-yl}-propionic acid. After preparative HPLC: 3-(1H-indol-2-yl)-3-{6-[3-(pyridin-2-ylamino)propoxy]-1H-indol-3-yl}propionic acid trifluoroacetate;

with thiophene-2-carbaldehyde and subsequent synthesis sequence gives

3-{6-[3-(pyridin-2-ylamino)propoxy]-1H-indol-3-yl}-3-thiophen-2-yl-propionic acid. After preparative HPLC: 3-{6-[3-(pyridin-2-ylamino)propoxy]-1H-indol-3-yl}-3-thiophen-2-ylpropionic acid trifluoroacetate;

with 1H-pyrrole-2-carbaldehyde and subsequent synthesis sequence gives

3-{6-[3-(pyridin-2-ylamino)propoxy]-1H-indol-3-yl}-3-(1H-pyrrol-2-yl)-propionic acid. After preparative HPLC: 3-{6-[3-(pyridin-2-ylamino)propoxy]-1H-indol-3-yl}-3-(1H-pyrrol-2-yl)propionic acid trifluoroacetate;

with thiazole-2-carbaldehyde and subsequent synthesis sequence gives

3-{6-[3-(pyridin-2-ylamino)propoxy]-1H-indol-3-yl}-3-thiazol-2-ylpropionic acid. After preparative HPLC: 3-{6-[3-(pyridin-2-ylamino)propoxy]-1H-indol-3-yl}-3-thiazol-2-ylpropionic acid trifluoroacetate;

with biphenyl-4-carbaldehyde and subsequent synthesis sequence gives 3-biphenyl-4-yl-3-{6-[3-(pyridin-2-ylamino)propoxy]-1H-indol-3-yl}-propionic acid. After preparative HPLC: 3-biphenyl-4-yl-3-{6-[3-(pyridin-2-yl-amino)propoxy]-1H-indol-3-yl}propionic acid trifluoroacetate;

with 6-dimethylamino-2-fluoro-3-formylbenzonitrile and subsequent synthesis sequence gives 3-(3-cyano-4-dimethylamino-2-fluorophenyl)-3-{6-[3-(pyridin-2-ylamino)propoxy]-1H-indol-3-yl}propionic acid. After preparative HPLC: 3-(3-cyano-4-dimethylamino-2-fluorophenyl)-3-{6-[3-(pyridin-2-ylamino)propoxy]-1H-indol-3-yl}propionic acid trifluoroacetate;

with 3-fluoro-4-trifluoromethylbenzaldehyde and subsequent synthesis sequence gives 3-(3-fluoro-4-trifluoromethyl phenyl)-3-{6-[3-(pyridin-2-ylamino)propoxy]-1H-indol-3-yl}propionic acid. After preparative HPLC: 3-(3-fluoro-4-trifluoromethylphenyl)-3-{6-[3-(pyridin-2-ylamino)propoxy]-1H-indol-3-yl}propionic acid trifluoroacetate;

with 4-isopropylbenzaldehyde and subsequent synthesis sequence gives 3-(4-isopropylphenyl)-3-{6-[3-(pyridin-2-ylamino) propoxy]-1H-indol-3-yl}-propionic acid. After preparative HPLC: 3-(4-isopropylphenyl)-3-{6-[3-(pyridin-2-ylamino) propoxy]-1H-indol-3-yl}propionic acid trifluoroacetate;

with cyclopropanecarbaldehyde and subsequent synthesis sequence gives 3-cyclopropyl-3-{6-[3-(pyridin-2-ylamino)propoxy]-1H-indol-3-yl}-propionic acid. After preparative HPLC: 3-cyclopropyl-3-{6-[3-(pyridin-2-yl-amino)propoxy]-1H-indol-3-yl}propionic acid trifluoroacetate;

with 2,2-dimethylpropionaldehyde and subsequent synthesis sequence gives 4,4-dimethyl-3-{6-[3-(pyridin-2-ylamino)propoxy]-1H-indol-3-yl}pentanoic acid. After preparative HPLC: 4,4-dimethyl-3-{6-[3-(pyridin-2-ylamino)propoxy]-1H-indol-3-yl}pentanoic acid trifluoroacetate;

with 2,2-dimethylbutyraldehyde and subsequent synthesis sequence gives 5,5-dimethyl-3-{6-[3-(pyridin-2-ylamino)propoxy]-1H-indol-3-yl}hexanoic acid. After preparative HPLC: 5,5-dimethyl-3-{6-[3-(pyridin-2-ylamino)propoxy]-1H-indol-3-yl}hexanoic acid trifluoroacetate;

EXAMPLE 23

Analogously to Example 1.7, ethyl 4-(2-ethoxycarbonyl-1-{6-[3-(pyridin-2-ylamino)propoxy]-1H-indol-3-yl}ethyl) benzoate, prepared analogously to Example 1.1–1.6, is stirred with dioxane/1N NaOH, giving 4-(2-carboxy-1-{6-[3-(pyridin-2-ylamino)propoxy]-1H-indol-3-yl}ethyl) benzoic acid.

EXAMPLE 24

Analogously to Example 18, the compound 35, prepared in accordance with Example 14.2, is reacted with 2-chloro- 3-nitropyridine and triethylamine, giving 3-{6-[3-(3-nitropyridin-2-ylamino)propoxy]-1H-indol-3-yl}-3-phenylpropionic acid. After preparative HPLC: 3-{6-[3-(3-nitropyridin-2-yl-amino)propoxy]-1H-indol-3-yl}-3-phenylpropionic acid trifluoroacetate.

TLC: Si-60, toluene/methanol 4:1, $R_f$=0.36; HPLC: (RP-18, gradient A:B from 99:1→1:99 in 1 hour) $R_t$=43.5 min; FAB-MS: (M+1)=461.

Reduction of the nitro group by catalytic hydrogenation (palladium/activated carbon, hydrogen, ethanol) gives 3-{6-[3-(3-aminopyridin-2-ylamino)propoxy]-1H-indol-3-yl}-3-phenylpropionic acid.

After preparative HPLC: 3-{6-[3-(3-aminopyridin-2-ylamino)propoxy]-1H-indol-3-yl}-3-phenylpropionic acid trifluoroacetate;

HPLC: (RP-18, gradient A:B from 99:1→1:99 in 1 hour) $R_t$=33.3 min; FAB-MS: (M+1)=431.

N-Acetylation of the amino group with the aid of acetic anhydride gives 3-{6-[3-(3-acetylaminopyridin-2-ylamino) propoxy]-1H-indol-3-yl}-3-phenylpropionic acid. After preparative HPLC: 3-{6-[3-(3-acetylaminopyridin-2-ylamino) propoxy]-1H-indol-3-yl}-3-phenylpropionic acid trifluoroacetate.

HPLC: (RP-18, gradient A:B from 99:1→1:99 in 1 hour) $R_t$=31.7 min; FAB-MS: (M+1)=473.

EXAMPLE 25

1. (3S)-3-Phenyl-3-{6-[3-(pyridin-2-ylamino)propoxy] indol-3-yl}propionic acid 46

50 g (0.113 mol) of ethyl 3-phenyl-3-{6-[3-(pyridin-2-ylamino)propoxy]indol-3-yl}propionate 7, prepared in accordance with Example 1, are separated into the two enantiomers by continuous chromatography on a modified cellulose support (Chiralcel OD-H) in isopropanol/n-heptane 30:70.

Yield: 24.5 g (98% of theory) of the active S enantiomer. HPLC: Chiralcel OD-H, i-propanol/n-heptane 30/70, $R_t$=14.08 min.

For ester cleavage, 24.4 g (55 mmol) of the S enantiomer are dissolved in 100 ml of ethanol and stirred for 12 hours at 60° C. with 110 ml (110 mmol) of 1N NaOH. When the reaction is complete, the reaction solution is allowed to cool and is acidified to pH 6 using 1N HCl. The resultant precipitate is filtered off with suction, washed with water and subsequently with MTB ether and dried, giving (3S)-3-phenyl-3-{6-[3-(pyridin-2-ylamino)propoxy]indol-3-yl}propionic acid.

m.p.: 137° C. HPLC: (RP-18, gradient A:B from 99:1→1:99 in 1 hour), where A=water+0.3% of TFA, B=acetonitrile/water+0.3% of TFA 4:1) $R_t$=31.1 min; chiral HPLC: Chirobiotic V, water (+1% of triethylammonium acetate/methanol 65:35, $R_t$=21.15 min.

2. (3S)-3-Phenyl-3-{6-[3-(pyridin-2-ylamino)propoxy] indol-3-yl}-propionic acid hydrochloride 2 g (4.8 mmol) of the internal salt 46 are dissolved in 5 ml of dioxane and stirred for 2 hours at RT with 20 ml (20 mmol) of 1N HCl. The solution is subsequently freeze-dried, giving (3S)-3-phenyl-3-{6-[3-(pyrid in-2-ylamino)propoxy] indol-3-yl}propionic acid hydrochloride.

Analysis: calculated: 66.4% C, 5.80% H, 9.30% N, 7.84% Cl found: 65.9% C, 5.91% H, 9.11% N, 7.44% Cl.

3. (3S)-3-Phenyl -3-{6-[3-(pyridin-2-ylamino)propoxy] indol-3-yl}-propionic acid methanesulfonate 2 g (4.8 mmol) of the internal salt 46 are dissolved in 5 ml of dioxane and stirred for 2 hours at RT with 310 µl (4.8 mmol) of methanesulfonic acid in 5 ml of water. The solution is subsequently evaporated, giving (3S)-3-phenyl-3-{6-[3-(pyridin-2-ylamino)propoxy]indol-3-yl}propionic acid methanesulfonate after freeze-drying from acetonitrile/water.

Analysis: calculated: 61.04% C, 5.71% H, 8.21% N, 6.26% S found: 60.90% C, 5.99% H, 8.01% N, 5.92% S.

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilized under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of an active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of an active ingredient of the formula I are introduced into hard gelatine capsules in a conventional manner in such a way that each capsule contains 20 mg of the active ingredient.

EXAMPLE H

Ampoules

A solution of 1 kg of an active ingredient of the formula I in 60 l of bidistilled water is sterile filtered, transferred into ampoules, lyophilized under sterile conditions and sealed under sterile conditions. Each ampoule contains 10 mg of active ingredient.

EXAMPLE I

Inhalation Spray 14 g of an active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:

1. A compound of the formula I

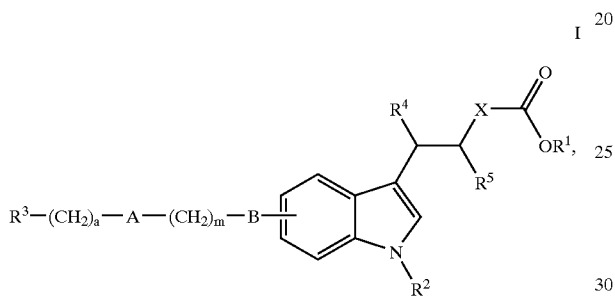

in which

A and B are each, independently of one another, O, S, NH, $NR^7$, CO, CONH, NHCO or a direct bond, X is alkylene having 1 to 2 carbon atoms which is unsubstituted or monosubstituted by $R^4$ or $R^5$, or a direct bond, $R^1$ is H, Z or —$(CH_2)_o$—Ar, $R^2$ is H, $R^7$ or —C(O)Z, $R^3$ is $Het^1$, $R^4$ and $R^5$ are each, independently of one another, H, oxo, $R^7$, —$(CH_2)_o$—Ar, —C(O)—$(CH_2)_o$—Ar, —C(O)—$(CH_2)_o$—$R^7$, —C(O)—$(CH_2)_o$—Het, Het, $NHR^6$, NHAr, NH—Het, CONH—$R^7$, CONH—$(CH_2)_o$—Ar, CONH—$(CH_2)_o$—Het, $OR^7$, OAr, $OR^6$ or O—Het, $R^6$ is H, —C(O)$R^7$, —C(O)—Ar, —C(O)—Het, $R^7$, $COOR^7$, COO—$(CH_2)_o$—Ar, COO—$(CH_2)_o$—Het, $SO_2$—Ar, $SO_2R^7$ or $SO_2$—Het, $R^7$ is alkyl having 1 to 10 carbon atoms or cycloalkyl having 3 to 10 carbon atoms, $R^8$ is Hal, $NO_2$, CN, Z, —$(CH_2)_o$—Ar, $COOR^1$, $OR^1$, $CF_3$, $OCF_3$, $SO_2R^1$, $NHR^1$, $N(R^1)_2$, NH—C(O)$R^1$, $NHCOOR^1$, COOH, COOZ or C(O)$R^1$, $R^9$ is CN or $NO_2$, Z is alkyl having 1 to 6 carbon atoms, Ar is aryl which is unsubstituted or monosubstituted or polysubstituted by $R^8$, Hal is F, Cl, Br or I, Het is unsubstituted indol-2-yl, pyrrol-2-yl, pyridin-4-yl, thiophen-4-yl, thiazol-2-yl or benzothiadiazole, each of which $Het^1$ is a pyridine, dihydropyridine or tetrahydropyridine, each of which may be unsubstituted or monosubstituted or disubstituted by Hal, $R^7$, $OR^7$, CN, NHZ, oxo or $NO_2$, n is 0, 1 or 2, m is 0, 1, 2, 3, 4, 5 or 6, and o is 0, 1 or 2, and physiologically acceptable salts and solvates thereof.

2. An enantiomer of a compound according to claim 1.

3. A compound according to claim 1, wherein X is a direct bond.

4. A compound according to claim 1, wherein

B is O, $R^4$ is $R^7$, $(CH_2)_o$—Ar or Het, o is 0 or 1, $R^5$ is H, and $R^7$ is alkyl having 1 to 10 carbon atoms or cycloalkyl having 3 to 10 carbon atoms.

5. A compound according to claim 1, selected from, a) 3-phenyl-3-{6-[3-(pyridin-2-ylamino)propoxy]-1H-indol-3-yl}propionic acid;

b) 3-phenyl-3-{6-[4-(pyridin-2-ylamino)butoxy]-1H-indol-3-yl}propionic acid;

c) 3-phenyl-3-{5-[4-(pyridin-2-ylamino)butoxy]-1H-indol-3-yl}propionic acid;

d) 3-phenyl-3-{5-[3-(pyridin-2-ylamino)propoxy]-1H-indol-3-yl}propionic acid;

e) 3-(4-fluorophenyl)-3-{6-[3-(pyridin-2-ylamino) propoxy]indol-3-yl}propionic acid;

f) 3-(3,5-dichlorophenyl)-3-{6-[3-(pyridin-2-ylamino) propoxy]indol-3-yl}propionic acid;

g) 3-(4-chloro-5-trifluoromethylphenyl)-3-{6-[3-(pyridin-2ylamino) propoxy]indol-3-yl}propionic acid;

h) 3-cyclohexyl-3-{6-[3-(pyridin-2-ylamino)propoxy] indol-3-yl}propionic acid;

i) 3-pyridin-4-yl-3-{6-[3-(pyridin-2-ylamino)propoxy] indol-3-yl}propionic acid;

j) 3-(3-chlorophenyl)-3-{6-[3-(pyridin-2-ylamino) propoxy]indol-3-yl}propionic acid;

k) 3-benzo-1,2,5-thiadiazol-5-yl-3-{6-[3-(pyridin-2-ylamino) propoxy]indol-3-yl}propionic acid;

l) 3-(3-hydroxyphenyl)-3-{6-[3-(3,4,5,6-tetrahydropyridin-2-yl amino) propoxy]indol-3-yl}propionic acid or m) 3-[4-methoxycarbonylphenyl]-3-{6-[3-(pyridin-2-ylamino) propoxy]indol-3-yl}propionic acid;

and physiologically acceptable salts and solvates thereof.

6. A process for the preparation of a compound according to claim 1 and its salts and solvates, wherein a) a compound of the formula I is liberated from one of its functional derivatives by treatment with a solvolyzing or hydrogenolyzing agent, or b) a radical $R^1$, $R^2$, $R^3$, $R^4$, $R^5$ and/or $R^6$ is converted into another radical $R^1$, $R^2$, $R^3$, $R^4$, $R^5$ and/or $R^6$, by i) converting an amino group into a guanidino group by reaction with an amidating agent, ii) saponifying an ester, iii) alkylating or acylating an amino group, iv) converting a cyano group into an amidino group, and/or a base or acid of the formula I is converted into one of its salts.

7. A therapeutic active ingredient comprising a compound according to claim 1 and physiologically acceptable salts or solvates thereof.

8. An integrin inhibitor comprising a compound according to claim 1 and physiologically acceptable salts or solvates thereof.

9. A pharmaceutical preparation, comprising at least one compound according to claim 1 and/or physiologically acceptable salts or solvates thereof.

10. A process for the preparation of a medicament comprising admixing a compound of according to claim 1 and/or physiologically acceptable salts or solvates thereof with at least one solid, liquid, or semi-liquid excipient or auxiliary or optionally, one or more other active ingredient.

11. A method of treating thromboses, cardiac infarction, coronary heart diseases, arteriosclerosis, inflammation, rheumatic arthritis, macular degenerative disease, diabetic retinopathy, tumour induced angiogenesis, tumor by inhibiting metastasis, tumor by initiation of apoptosis osteoporosis, and/or infections and restenosis after angioplasty comprising administering to a patient in need thereof therapeutic effective amount of the a compound according to claim 1 and/or physiologically acceptable salts or solvates thereof.

12. A compound according to claim 1, wherein
$Het^1$ is
3-nitropyridin-2-yl,
3-aminopyridin-2-yl,
3-(N-acetylamino)pyridin-2-yl,
pyridin-2-yl,
or
1,4,5,6-tetrahydropyridin-2-yl.

13. A compound according to claim 1, wherein
$Het^1$ is
2-, 3- or 4-pyridyl,
1,4-dihydro-1-, -2-, -3- or -4-pyridyl,
1,2,3,4-tetrahydro-1-, -2-, -3-, -4-, -5- or -6-pyridyl,
or
1,2,3,6-tetrahydro-1-, -2-, -3, -4-, -5- or -6-pyridyl.

14. A compound according to claim 1, wherein $R^1$ is H.

15. A compound according to claim 1, wherein $R^4$ is phenyl, 3-trifluoro methoxy phenyl, 4-fluorophenyl, 3-chlorophenyl, 3-hydroxyphenyl, pyridin-4-yl, 3,5-dichloro phenyl, 2,4-dichlorophenyl, cyclohexyl, 4-chloro-3-trifluoromethylphenyl, benzo thiadiazol-4-yl, 2,6-difluorophenyl, 2-chloro-3,6-difluorophenyl, 2,4,6-trifluorophenyl or cyclohexyl.

16. A compound according to claim 1, wherein $R^5$ is H.

17. A compound according to claim 1, wherein $R^6$ is H, methoxycarbonyl, ethoxycarbonyl, tert-butoxycarbonyl or benzyloxycarbonyl.

18. A compound according to claim 1, wherein $R^2$ is H, methyl or acetyl.

19. A compound according to claim 1, wherein $Het^1$ is pyridine.

* * * * *

UNITED STATES PATENT AND TRADEMARK OFFICE
CERTIFICATE OF CORRECTION

PATENT NO. : 6,743,810 B2
APPLICATION NO. : 10/203406
DATED : June 1, 2004
INVENTOR(S) : Simon Goodman It is certified that error appears in the above-identified patent and that said Letters Patent is hereby corrected as shown below:

Column 43, line 62, reads "benzothiadiazole, each of which" should read -- benzothiadiazole --
Column 44, line 31, reads "(pyridin-2ylamino)" should read -- (pyridin-2-ylamino) --
Column 44, line 43, reads "propionic acid or" should read -- propionic acid; or --
Column 45, line 5, reads "a compound of according" should read -- a compound according --
Column 45, line 10, reads "inflammation," should read -- inflammations, --
Column 45, line 13, reads "apoptosis" should read -- apoptosis, --
Column 45, line 16, reads "therapeutic effective" should read -- a therapeutically effective --
Column 45, line 16, reads "of the a compound" should read -- of a compound --

Signed and Sealed this

Twenty-fifth Day of August, 2009

David J. Kappos
*Director of the United States Patent and Trademark Office*